(12) United States Patent
Chu et al.

(10) Patent No.: US 9,541,475 B2
(45) Date of Patent: Jan. 10, 2017

(54) METHODS AND APPARATUS FOR DETECTING PARTICLES ENTRAINED IN FLUIDS

(75) Inventors: Winnie Chu-Hui Chu, Lions Bay (CA); Allison Schaap, Burnaby (CA); Boris Stoeber, Vancouver (CA)

(73) Assignee: The University of British Columbia, Vancouver (CA)

( * ) Notice: Subject to any disclaimer, the term of this patent is extended or adjusted under 35 U.S.C. 154(b) by 555 days.

(21) Appl. No.: 13/882,092

(22) PCT Filed: Oct. 28, 2011

(86) PCT No.: PCT/CA2011/050681
§ 371 (c)(1),
(2), (4) Date: Apr. 26, 2013

(87) PCT Pub. No.: WO2012/055048
PCT Pub. Date: May 3, 2012

(65) Prior Publication Data
US 2013/0213115 A1    Aug. 22, 2013

Related U.S. Application Data

(60) Provisional application No. 61/408,561, filed on Oct. 29, 2010.

(51) Int. Cl.
*G01N 15/00* (2006.01)
*G01N 1/28* (2006.01)
(Continued)

(52) U.S. Cl.
CPC . *G01N 1/28* (2013.01); *B07B 7/00* (2013.01); *G01N 15/0255* (2013.01); *G01N 2001/2223* (2013.01); *G01N 2015/0088* (2013.01)

(58) Field of Classification Search
CPC ............... G01N 15/0255; G01N 2015/0261; B07B 7/02; B07B 7/086
See application file for complete search history.

(56) References Cited

U.S. PATENT DOCUMENTS 2,732,753 A    1/1956  O'Konski
2,920,525 A *  1/1960  Appel ................. G01N 21/255
                                              250/564
(Continued)

OTHER PUBLICATIONS

Oozeki, N. et al., "Characterization of Microseparator/Classifier with a Simple Arc Microchannel", AIChE Journal, vol. 55, No. 1, Jan. 2009, pp. 24-34.

(Continued)

*Primary Examiner* — Laura Martin
*Assistant Examiner* — Alex Devito
(74) *Attorney, Agent, or Firm* — Oyen Wiggs Green & Mutala LLP

(57) ABSTRACT

Apparatus and methods for size-specific detection of particles entrained in fluids are provided. A particle size selector separates particles entrained in a sample fluid stream using a curved channel. Shroud fluid streams are interposed between the sample fluid stream and walls of the channel. Centrifugal forces arising from fluid flow through the curved channel separate differently-sized particles into different transverse sections of the channel. A detector downstream from the particle size selector specifically detects particles in one or more transverse sections of the channel.

59 Claims, 15 Drawing Sheets

(51) Int. Cl.
    *G01N 15/02*    (2006.01)
    *B07B 7/00*    (2006.01)
    *G01N 1/22*    (2006.01)

(56) References Cited

U.S. PATENT DOCUMENTS

| | | | | |
|---|---|---|---|---|
| 3,361,030 | A | | 1/1968 | Goldberg |
| 3,710,933 | A | * | 1/1973 | Fulwyler ............... G01N 15/12 209/3.1 |
| 4,153,541 | A | | 5/1979 | Rumpf et al. |
| 4,383,917 | A | | 5/1983 | Wells |
| 4,872,972 | A | | 10/1989 | Wakabayashi et al. |
| 4,928,153 | A | * | 5/1990 | Glass .................... G01N 21/47 356/343 |
| 5,498,273 | A | * | 3/1996 | Mann ........................ B04C 3/06 55/396 |
| 6,091,502 | A | * | 7/2000 | Weigl ............... G01N 27/44721 356/416 |
| 6,592,822 | B1 | * | 7/2003 | Chandler ........... G01N 15/1456 356/72 |
| 7,473,216 | B2 | | 1/2009 | Lolachi et al. |
| 2007/0178529 | A1 | * | 8/2007 | Breidford ............... B01F 11/04 435/7.1 |
| 2009/0050538 | A1 | * | 2/2009 | Lean .................... B01D 21/265 209/155 |
| 2009/0283456 | A1 | | 11/2009 | Le Vot et al. |

OTHER PUBLICATIONS

Gossett, D.R. et al., "Particle Focusing Mechanisms in Curving Confined Flows", Anal. Chem. 2009, 81, pp. 8459-8465.

Seo, J. et al., "Membraneless microseparation by asymmetry in curvilinear laminar flows", Journal of Chromatography A, vol. 1162, 2007, pp. 126-131.

Ookawara, S. et al., "Feasibility study on concentration of slurry and classification of contained particles by microchannel", Chemical Engineering Journal, vol. 101, 2004, pp. 171-178.

Committee on the Medical Effects of Air Pollutants, "Cardiovascular Disease and Air Pollution", UK Department of Health, Feb. 2006.

Pope, C.A. et al., "Lung cancer, Cardiopulmonary Mortality, and Long-term Exposure to Fine Particulate Air Pollution", JAMA, Mar. 2002, vol. 287, No. 9, pp. 1132-1141.

Bell, M.L. et al., Reassessment of the Lethal London Fog of 1952: Novel Indicators of Acute and Chronic Consequences of Acute Exposure to Air Pollution, Environmental Health Perspectives, vol. 109, supplement 3, Jun. 2001, pp. 389-394.

Ostro, B., "Assessing the environmental burden of disease at national and local levels", WHO Environmental Burden of Disease Series, No. 5, Geneva, 2004, World Health Organization.

U.S. Environmental Protection Agency, "Fine Particle (PM2.5) Designations: Frequent Questions", vol. 2010, 2008, http://www.epa.gov/pmdesignations/faq.htm.

World Health Organization, "Air Quality Guidelines particulate matter, ozone, nitrogen dioxide and sulfur dioxide: Global update 2005", 2005.

Walton, W.H. et al., "Aerosol Instrumentation in Occupational Hygiene: An Historical Perspective", Aerosol Science and Technology, vol. 28, 1998, pp. 417-438.

Chua, B. et al., "Electrical Mobility Separation of Airborne Particles Using Integrated Microfabricated Corona Ionizer and Separator Electrodes", Journal of Microelectromechanical Systems, vol. 18, Feb. 2009, pp. 4-13.

Moon, H.S. et al., "Continuous microfluidic airborne bacteria separation using dielectrophoresis", Transducers, Jun. 21-25, 2009, pp. 2038-2041.

* cited by examiner

METHODS AND APPARATUS FOR DETECTING PARTICLES ENTRAINED IN FLUIDS

REFERENCE TO RELATED APPLICATION

This application claims the benefit of the priority of U.S. application No. 61/408,561 filed 29 Oct. 2010 and entitled MICROCHANNEL BASED METHODS AND APPARATUS FOR DETECTING AIRBORNE PARTICLES which is hereby incorporated herein by reference. For the purpose of the United States this application claims the benefit of the provisions of 35 USC §119(e) with respect to U.S. application No. 61/408,561.

FIELD OF THE INVENTION

The invention relates to the detection of particles entrained in fluid. Some embodiments provide methods and apparatus for detecting airborne particles. Some embodiments have application in monitoring environmental air quality. Some embodiments provide wearable detectors for measuring exposure of personnel to inhalable particles and associated methods.

BACKGROUND

Inhalation of airborne particles ("aerosols") causes a wide range of negative health effects. The toxicity of aerosols depends on their physical form and size. Long-term and short-term exposure to particulate air pollution has been linked to increased cardiopulmonary mortality, lung cancer, asthma, heart failure, and other cardiovascular diseases. The World Health Organization (WHO) estimates that exposure to outdoor air pollution is responsible for 1.4% of global mortalities and 2% of cardiopulmonary disease. This well-proven link has led to the development of exposure limits and air pollution regulations by organizations including the US Environmental Protection Agency and the WHO, who recommend that long-term exposure to PM2.5 (airborne particulate matter of diameter<2.5 µm) not exceed 15 µg/m$^3$ and 10 µg/m$^3$ respectively.

Different applications of aerosol exposure monitoring present different needs. The WHO recommends monitoring PM2.5 exposure over several years in fixed-site monitors, particularly throughout metropolitan areas. Occupational health studies may require monitoring numerous specific individuals over long time periods.

Current particle monitoring technology is typically prohibitively expensive for performing high resolution geographic monitoring and too large and cumbersome to be carried conveniently by individuals. Continuous personal exposure monitoring and geographically-distributed environmental monitoring applications require a sensor that is smaller and lower in cost than existing devices and at least capable of measuring the levels of PM2.5.

Currently available commercial technologies used in environmental monitoring and occupational health applications include gravimetric samplers, in which a known volume of sample air is drawn through a filter that is weighed before and after the measurement. Gravimetric sampling may be used in combination with impactors and cyclones, which select for particle size by causing sudden changes of direction in flow streamlines such that smaller particles continue with the flow and larger ones cross the streamlines to impact on a surface or pass through an orifice. Gravimetric techniques have the advantage of simplicity and of collecting sample for later chemical analysis; however, they require careful and time-consuming pre- and post-weighing of the filter and do not allow the real-time measurement of data.

A modern gravimetric technique for monitoring for airborne particles uses a tamper element oscillating microbalance (TEOM). A TEOM measures aerosol mass directly and in real-time, but is expensive and, currently, only available in a large static package.

Other approaches include optical sensors, some of which first increase the apparent size of particles by passing them through a condensing liquid, and which rely on the scattering of laser light to size and count individual particles.

Electrostatic separators and detectors cause particles to become electrically charged, and then select for particle size by manipulating the balance of electrostatic forces and physical inertia. These devices also provide continuous real-time data, but require long columns with high voltages to provide good size resolution.

Airborne particles have also been sorted in a microchannel by dielectrophoresis, but this approach required the introduction of airborne particles into liquid and significant sample preparation before sorting could occur.

The following are some publications in the general field of the invention:

Committee on the Medical Effects of Air Pollutants, "*Cardiovascular Disease and Air Pollution,*" UK Department of Health, 2006.

C. A. Pope, R. T. Burnett, M. J. Thun, E. E. Calle, D. Krewski, K. Ito and G. D. Thursten, "Lung cancer, cardiopulmonary mortality, and long-term exposure to fine particulate air pollution," J. Am. Med Assoc., vol. 287, pp. 1132, 2002.

M. L. Bell and D. L. Davis, "Reassessment of the lethal London fog of 1952: novel indicators of acute and chronic consequences of acute exposure to air pollution.

"Environ. Health Perspect., vol. 109, pp. 389-394, 2001. B. Ostro, "Assessing the environmental burden of disease at national and local levels," WHO Environmental Burden of Disease Series, no. 5, vol. Geneva, World Health Organization, 2004.

U.S. Environmental Protection Agency, "Fine Particle (PM2.5) Designations: Frequent Questions," vol. 2010, 2008.

World Health Organization, "WHO Air quality guidelines for particulate matter, ozone, nitrogen dioxide and sulfur dioxide: Global update 2005," 2005.

W. H. Walton and J. H. Vincent, "Aerosol Instrumentation in Occupational Hygiene: An Historical Perspective," Aerosol Science and Technology, vol. 28, pp. 417, 1998.

B. Chua, A. S. Wexler, N. C. Tien, D. A. Niemeier and B. A. Holmen, "Electrical Mobility Separation of Airborne Particles Using Integrated Microfabricated Corona Ionizer and Separator Electrodes," Microelectromechanical Systems, Journal of, vol. 18, pp. 4-13, 2009.

H. S. Moon, Y. W. Nam, J. C. Park and H. I. Jung, "Continuous microfluidic airborne bacteria separation using dielectrophoresis," pp. 2038, 2009.

Jeonggi Seo et al., *Membraneless microseparation by asymmetry in curvilinear laminar flows*, Journal of Chromatography A, 1162 (2007) 126-131;

Daniel R. Gossett and Dino Di Carlo, *Particle Focusing Mechanisms in Curving Confined Flows*, Anal. Chem. 2009, 81, 8459-8465;

Shinichi Ookawara et al., *Feasibility study on concentration of slurry and classification of contained particles by microchannel*, Chemical Engineering Journal 101 (2004) 171-178;

Nobuo Oozeki et al., *Characterization of Microseparator/Classifier with a Simple Arc Microchannel*, AIChE Journal, January 2009 Vol. 55, No. 1.

Some patent documents in the field of the invention are: LeVot et al. US 2009/0283456.

There is a need for practical and cost-effective methods and apparatus for detecting and/or measuring particles entrained in fluid, such as air, for example. Some applications require such apparatus and methods that are compact and readily portable.

SUMMARY OF THE INVENTION

The invention has a number of aspects.

An aspect of the invention provides a size-specific particle detection apparatus. The apparatus comprises a particle size selector having a channel having a curved section, a sample fluid introduction port upstream of the curved section, and at least one shroud fluid port upstream of the curved section. The sample fluid introduction port and the at least one shroud fluid port are configured to interpose a shroud fluid stream introduced via the at least one shroud fluid port between a sample fluid stream introduced via the sample fluid introduction port and the outside of the curved section. A detector is configured to detect particles in the channel downstream from a start of the curved section. The detector may be configured to specifically detect particles in a transverse section of the channel. In some embodiments, the channel may widen after the curved section; the detector may be located in a widened section of the channel. In some embodiments, the channel has a divider downstream of the curved section defining a plurality of sub-channels; the detector may be located in one of such sub-channels.

In some embodiments, the at least one shroud fluid port comprises an outside shroud fluid port configured to introduce shroud fluid along a side of the channel leading to the outside of the curved section. The sample fluid introduction port and the at least one shroud fluid port may be configured to interpose a shroud fluid stream introduced via the at least one shroud fluid port between the sample fluid stream introduced via the sample fluid introduction port and the inside of the curved section. In some embodiments, the apparatus comprises a source of pressurized shroud fluid connected to the at least one shroud fluid port, such as an air pump and a filter connected to filter air pumped by the air pump, a source of compressed gas, or the like.

Another aspect of the invention provides a method for separating particles entrained in a sample fluid stream according to particle size. The method comprises flowing the sample fluid stream through a curved section of a channel with the sample fluid stream spaced apart from the outside of the curved section by shroud fluid to separate the particles into a plurality of different transverse sections of the channel. Some embodiments according to this aspect comprise sandwiching the sample fluid stream between streams of shroud fluid upstream from the curved section.

A further aspect of the invention provides a method for size-specific detection of particles in a sample fluid stream. The method comprises flowing the sample fluid stream through a curved section of a channel with the sample fluid stream spaced apart from the outside of the curved section by shroud fluid to separate the particles into a plurality of different transverse sections of the channel, and detecting particles downstream from the curved section at one or more of the different transverse sections of the channel. Some embodiments according to this aspect comprise sandwiching the sample fluid stream between streams of shroud fluid upstream from the curved section. Shroud fluid may be introduced downstream from the curved section to laterally displace fluid flowing in the channel. Some embodiments according to this aspect comprise specifically detecting particles in the one or more transverse sections of the channel.

Yet another aspect of the invention provides a particle size selector comprising a channel having a curved section, a sample fluid introduction port upstream of the curved section, and at least one shroud fluid port upstream of the curved section, the sample fluid introduction port and the at least one shroud fluid port configured to interpose a shroud fluid stream introduced via the at least one shroud fluid port between a sample fluid stream introduced via the sample fluid introduction port and the outside of the curved section.

Further aspects of the invention and features of example embodiments are illustrated in the accompanying drawings and the following detailed descriptions.

BRIEF DESCRIPTION OF THE DRAWINGS

The accompanying drawings illustrate non-limiting example embodiments of the invention.

DETAILED DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The invention provides particle detection methods and apparatus which performs size-selection of particles at least in part by passing the particles through a curved section of a channel. The invention may be embodied in a wide range of apparatus suitable for different applications in which detection and/or measurement of particles entrained in fluid (e.g., airborne particles) are required. Example applications include: environmental air quality monitoring (either for short terms or for extended periods, outdoor or in buildings such as homes or workplaces); personal exposure monitoring; monitoring the efficacy of air filtration on HVAC (heating ventilating air conditioning) applications; and particle sorting in bioanalytics applications (e.g., magnetic particles for drug delivery).

Figure 1:
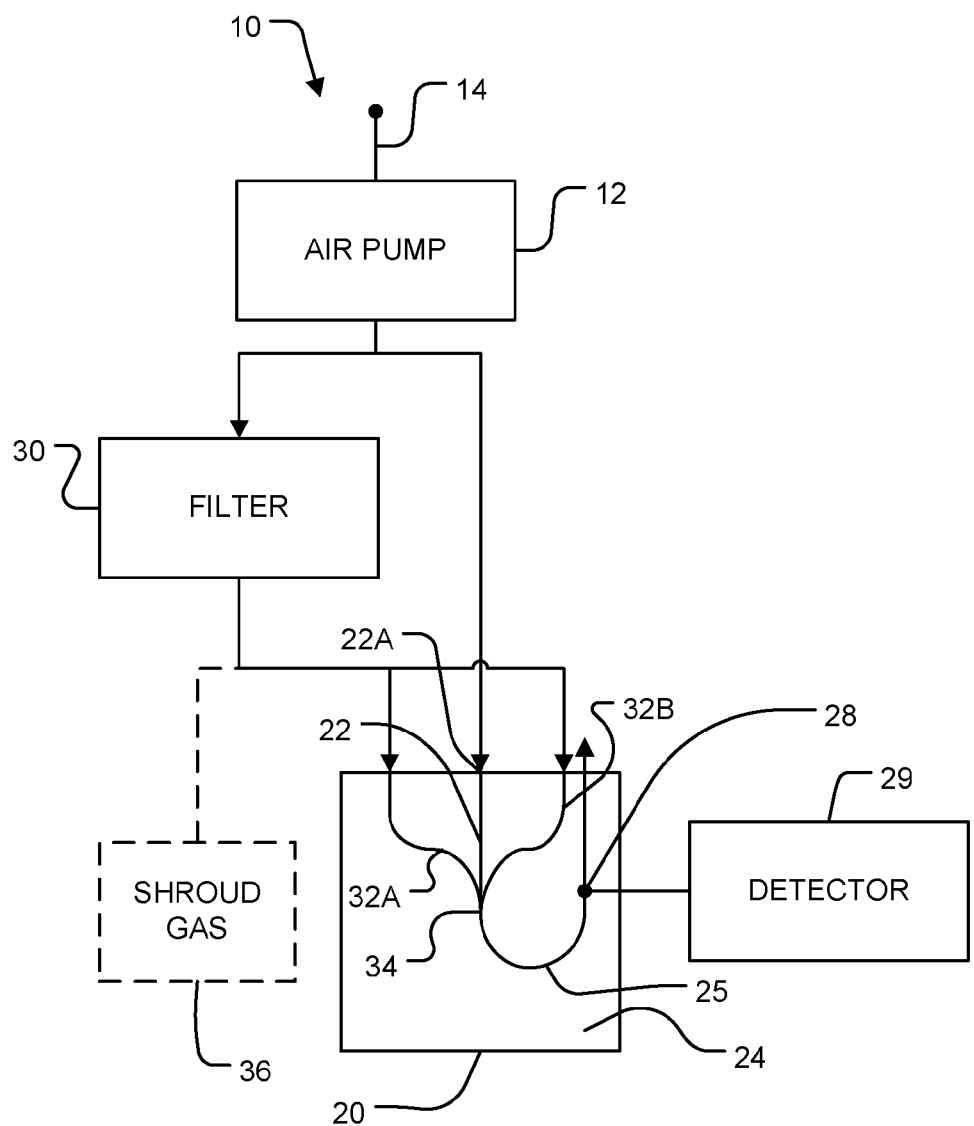
FIG. 1 is a block diagram illustrating apparatus according to an example embodiment of the invention.

FIG. 1 shows a monitoring apparatus 10 according to an example embodiment. Apparatus 10 comprises an air pump 12 that takes in air at an inlet 14 and delivers the air to a microchannel particle size selector 20. Particle size selector 20 comprises a channel 22 formed in a substrate 24. In the illustrated embodiment, channel 22 is a microchannel; in other embodiments, channel 22 may be a minichannel or other type of channel. A portion 25 of microchannel 22 is curved. In the illustrated embodiment, portion 25 includes a hairpin bend (in which microchannel 22 turns through an angle of about 180 degrees).

In operation, a flow of air which may contain particles of interest is introduced to microchannel 22 at a sample fluid introduction port 22A and carried through microchannel 22. As any entrained particles pass through curved section 25 the particles experience centrifugal forces. The forces result in differential motion of the particles within the flowing air such that the particles become separated by size as they pass through curved portion 25. One or more particle sensors 28 is located downstream from curved section 25 (or at least far enough downstream from the start of curved section 25 for adequate particle size separation to have occurred). Sensor 28 senses particles of interest that are being carried along microchannel 22 and detector circuitry 29 receives and processes an output of sensor(s) 28.

In the illustrated embodiment, shroud gas is introduced into microchannel 22 at a junction point 34. Junction point 34 is downstream from sample fluid introduction port 22A. Shroud gas is introduced to microchannel 22 at junction point 34 via a pair of shroud fluid ports 32A and 32B, located along sides of microchannel 22 leading, respectively, to the outside and inside of curved section 25. In the illustrated embodiment, shroud ports 32A and 32B comprise channels that extend from junction 34 to the exterior of particle size selector 20, but other shroud ports configurations are possible.

In the illustrated embodiment the shroud gas is supplied by filtering air pumped by air pump 12 through a filter 30 that removes any particles of interest from the shroud air. Filter 30 may comprise a HEPA filter for example. Shroud air that has been filtered by filter 30 is carried to junction 34 by passages 32.

Shroud gas may be provided by a separate gas source (such as a source of a compressed gas such as dry nitrogen or the like). FIG. 1 shows an optional gas source 36.

The provision of a shroud gas on either side of the particle-laden air being carried in microchannel 22 causes the particle-laden air to be carried into the middle of microchannel 22 sandwiched between layers of flowing shroud gas which are substantially free of particles of interest. When the gases pass through curved section 25 particles being carried in the gas flowing in the middle portion of microchannel 22 are affected by forces including centrifugal forces in a way that causes size-segregation of the particles in a direction across the microchannel. Particles having sizes in a size range of interest can be detected downstream from curved section 25 by monitoring for particles at a specific transverse location in microchannel 22 using a suitable sensor 28.

Pump 12 may be of any of a wide variety of types. Advantageously, pump 1 is of a type that produces a steady (not strongly pulsatile) flow. For example, pump 12 may comprise a suitable membrane pump. In some embodiments, separate pumps are provided for shroud air and for the air that is directed along microchannel 22.

The dimensions of the microchannel 22 and shroud ports 32A and 32B may be varied. In some embodiments the widths of shroud ports 32A and 32B are the same as or wider than the width of microchannel 22.

Theory and Principle

While the inventors do not wish to be bound by any particular theory of operation, it is currently believed that the following description explains underlying principles of operation of apparatus as described herein.

A. Particle Separation

As noted above, airborne particles of different sizes are separated using the centrifugal force generated when they travel around a bend. Airborne particles are focused towards the center of a microchannel (e.g. by introducing a shroud gas) before the particles travel around a curved section of the channel. In the curved portion of the channel, competing centrifugal and viscous forces lead to a radially outward size-dependent displacement of the particles.

For a sphere of density ρ and diameter d moving in an arc of radius r with velocity V, the centrifugal force is given by:

$$F_{centrifugal} = \frac{mV^2}{r} = \frac{\pi \rho d^3 V^2}{6r} \tag{1}$$

The centrifugal force acts to push the sphere away from the center of the arc, causing it to cross the fluid streamlines. The cross-streamline motion of a particle due to the centrifugal force is opposed by viscous forces acting against the particle's cross-streamline motion, as expressed by Stokes' Law which is given by:

$$F_{viscous} = 3\pi\mu U d \tag{2}$$

where μ is the fluid viscosity and U represents the difference in velocity between the particle and the fluid.

The particle's axial velocity is taken as being the same as the fluid's, so U is simply the particle's cross-streamline radial velocity. The behaviour of an individual particle can be predicted if the flow rates of shroud and sample air and the flow profile in the separation channel are known.

Figure 2:
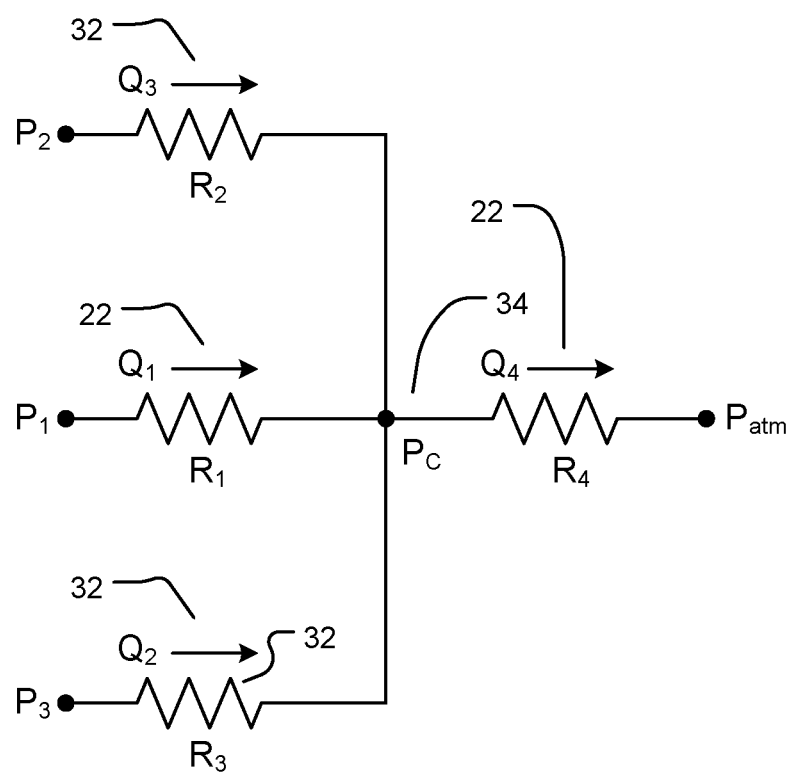
FIG. 2 is a resistor network analogy to a microfluidic system according to an example embodiment.

The flow rates $Q_i$ of the shroud and sample air as a function of the driving pressures $P_i$ and of the channel width $W_i$ and height $H_i$ can be calculated from the channel flow resistances $R_i$ per length of channel section $L_i$ by the following equation:

$$\frac{R_1}{L_i} = \frac{\Delta P_i}{Q_i L_i} = \frac{12\mu}{H_i W_i^3 \left[1 - 0.63\left(\frac{W_i}{H_i}\right)\right]} \quad (3)$$

and a fluidic version of Ohm's Law. FIG. 2 shows an electrical analogy to the resistances provided by shroud gas channels 32 and the portions of microchannel 22 upstream and downstream from junction point 34. Determination of flow rates in microfluidic systems is described, for example, in P. Tabeling, *Introduction to Microfluidics*, United Kingdom: Oxford University Press, 2005 which is hereby incorporated herein by reference.

For four channels which connect at one node, the total mass flow into the node must be equal to the mass flow out, providing the relationship between the flow rates, inlet pressures and channel flow resistances $$\frac{(P_1 - P_C)}{R_1} + \frac{(P_2 - P_C)}{R_2} + \frac{(P_3 - P_C)}{R_3} = \frac{(P_C - P_{atm})}{R_4} \quad (4)$$

with $P_C$ the pressure at the node joining the inlets to the outlet and $P_{atm}$ the atmospheric pressure at the outlet. $R_1$, $R_2$, and $R_3$ are the sample and shroud channel fluidic resistances, as calculated by Equation 3 above. $R_4$ is the outlet channel resistance plus any other fluidic resistances; for example, that of a filter collecting particles at the channel exit. Solving for $P_C$ gives the flow rates of the shroud and sample lines, as well as in the separation section.

The velocity profile of the flow in the channel may be estimated by applying the no-slip condition as a boundary condition to the Navier Stokes equations. One such solution—using a first-order no-slip boundary condition—is:

$$u_X(y, z) = \frac{16}{\pi^4} \frac{\Delta P}{\mu L} \sum_n^\infty \sum_m^\infty \frac{1}{nm\left(\frac{n^2}{W^2} + \frac{m^2}{H^2}\right)} \sin\left(\frac{n\pi y}{W}\right) \sin\left(\frac{m\pi z}{H}\right) \quad (5)$$

for odd integers n and m, where y and z represent the position in the channel cross-section along the height and width respectively, with (0, 0) at the bottom left corner of the channel when looking downstream. The resulting flow profile inside the channel shows zero velocity at the walls (from the imposed no-slip condition) with the maximum velocity in the center of the channel.

By using the flow resistance model above to find the volumetric flow rates through each of the inlet channels and considering the flow profile in the main channel, the width of each shroud section in the main channel may be estimated by integrating from the outer edges towards the center of the channel until the integral equals the flow rate of that section. The sample width is the total width minus the two shroud widths.

B. Diffusion

Small particles in air are affected by Brownian motion, caused by small forces imparted to the particles by the constant motion of the air molecules. The result is a time-dependent stochastic diffusion process by which a region of concentrated particles will gradually spread out. In two dimensions, the resulting conditional probability that a particle located at position (y, z)=(0, 0) at time t=0 will be found at position (y, z) at time t is given by:

$$P(y, z, t, 0, 0) = \frac{1}{\sqrt{8\pi Dt}} \exp\left(-\frac{y^2 + z^2}{8Dt}\right) \quad (6)$$

This is a normal distribution with a mean of zero and a standard deviation $\sigma = \sqrt{4Dt}$. The translational diffusion coefficient given by:

$$D = \frac{k_B T C_S}{3\pi\mu d} \quad (7)$$

of the particle depends on the particle and fluid characteristics as well as on the Boltzmann constant $k_B$, the temperature T in Kelvin, and the Cunningham slip correction factor which is given by:

$$C_S = 1 + \frac{2\lambda}{d}\left(A_1 + A_2 \exp\left(\frac{A_3 d}{\lambda}\right)\right) \quad (8)$$

for the constants $A_1=1.257$, $A_2=0.40$ and $A_3=0.55$ and $\lambda$ the mean free path of an air molecule. The Cunningham slip correction factor is a correction to the drag force predicted by the Stokes equations, used when particles are sufficiently small, or the fluid pressure sufficiently low, that the medium in which particles travel may no longer appear fully continuous. For spherical particles traveling in room temperature air, the Cunningham slip correction factor is $C_S=1.52$ for 0.5 μm diameter particles and $C_S=1.085$ for 3.0 μm diameter particles.

C. Simulations

The behaviour of particles in the microchannels of a separation apparatus as described above may be simulated using tools such as MATLAB™. This may be done, for example, by generating a model in which particles are distributed evenly across the sample air at the inlet of a microchannel 22. Each individual particle is followed along the channel in small time intervals; at each interval, the local fluid velocity determines the balance of forces on the particle and a resulting new particle position is calculated, and then a random step from Brownian motion is imposed on the particle's position. The Brownian motion step is simulated with a double random walk approach $$\begin{cases} \alpha = rand(0, 2\pi) \\ \beta = normrnd(0, \sqrt{4D\Delta t}) \\ \Delta z_B = \beta \cos(\alpha) \\ \Delta y_B = \beta \sin(\alpha) \end{cases} \quad (9)$$

where rand(0,2π) represents a random number chosen between 0 and 2π, and normrnd(0,√4DΔt) represents a random number chosen with the a normal probability density function with mean 0 and standard deviation √4DΔt.

The combination of the Brownian motion model with the balance of the forces in (1) and (2) yields the change in position of the particle at each time interval $$\begin{cases} \Delta x = V(y,z)\Delta t \\ \Delta y = \Delta y_B \\ \Delta z = \frac{1}{18}\left(\frac{\rho d^2 V(y,z)^2}{r\mu}\right)\Delta t + \Delta z_B \end{cases} \quad (10)$$

with x, y, and z the position of the particle in the channel's length, height and width directions respectively. At the end of the channel, the particle's position is recorded and added to a simulated image of the channel cross-section.

Figure 3:
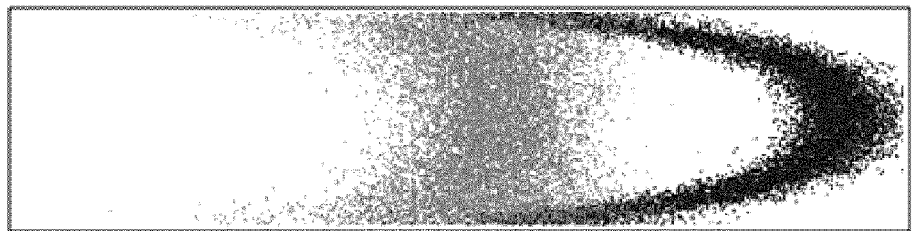
FIGS. 3 and 4 are plots showing the results of simulations based on mathematical models of the movement and diffusion of particles.
Figure 4:
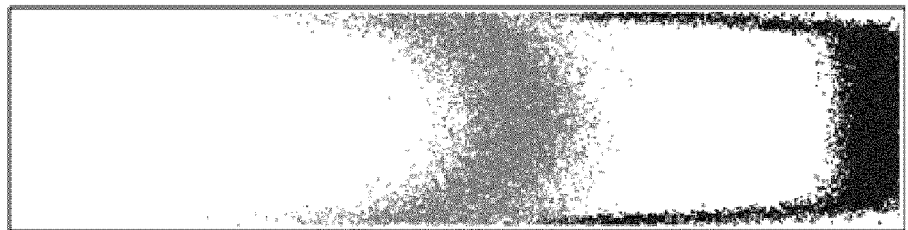

FIGS. 3 and 4 show results of such simulations in which 0.75 μm particles (shown as light green) and 2.88 μm particles (shown as dark blue) are modeled undergoing separation and diffusion. In FIG. 3A v=0.2 m/s. In FIG. 3B, v=0.5 m/s. A ratio of total shroud flow to sample flow in each case was 10:1, with shroud flow introduced by symmetric ports. FIGS. 3A and 3B are not-to-scale.

Example Prototype Embodiment

A. Channel Fabrication and Characterization

Microchannels for characterization and separation experiments were fabricated using standard photolithography techniques. The photolithography process (using SU-8 3050, Microchem Corp.), produced a negative mold of the channel. The mold was then used to form channels made of polydimethylsiloxane (PDMS), a two-component silicone polymer. The PDMS (Sylgard® 184, Dow Corning), was combined in a ratio of 10 parts base to 1 part hardener before being mixed and poured on the mold ("Piece A"). A second piece was prepared by pouring approximately 10 mL of PDMS onto a glass microscope slide with side walls formed with aluminum foil; this piece forms the fourth channel wall ("Piece B"). The two pieces of PDMS were degassed, cured in an oven at 80° C. for 2.5 hours, and then peeled off from their respective substrates. Holes were punched through Piece A to provide access to the channel inlets. Both pieces were treated with an oxygen plasma for 45 s (Expanded Plasma Cleaner on "high" setting, Harrick Plasma) and the flat side of Piece B was pressed against the channel side of Piece A. The combined PDMS part was transected through the channel near the outlet to allow a piece of filter paper (MetriCEL mixed cellulose ester membrane, 0.8 μm pore, Pall Scientific) to be placed into the path of the particles which travelled along the channel during experiments. After the particles were captured, the filter was removed and examined on a microscope (Eclipse TE2000-U inverted microscope, Nikon Corp.) for imaging of the particle locations.

Figure 5:
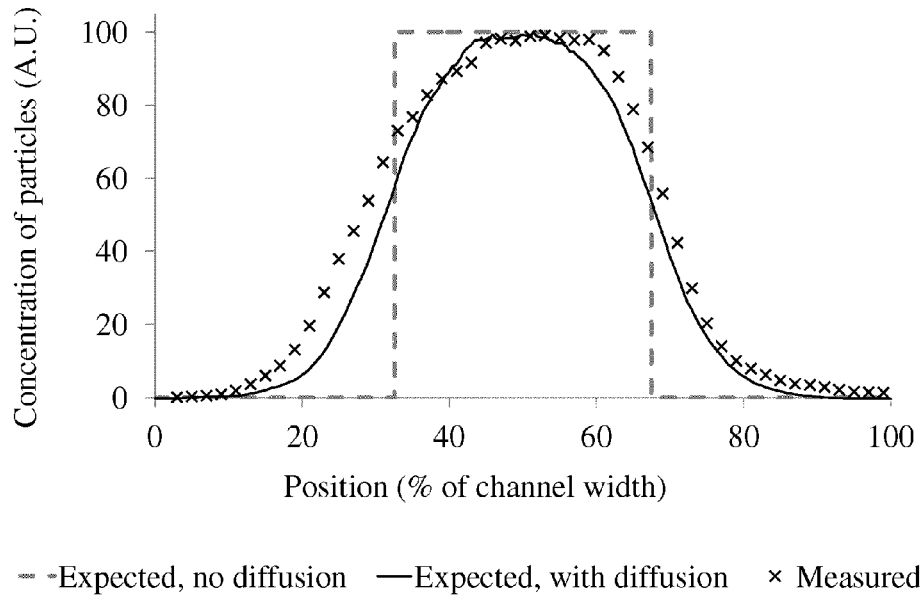
FIG. 5 is a graph showing predicted and measured particle distributions.

Two types of channels were fabricated for experiments. The first were straight channels, used to verify the flow resistance of the channels and the shroud to sample ratio resulting from various inlet pressures, and to observe the cross-streamline diffusion of particles. Channels with a curved main section for separation were also made to test the separation of particles by size (FIG. 5). In these prototypes, the channels are 100 μm high, with shroud inlets 40 μm wide and the main section 60 μm wide. The curved section had a 5 mm radius of curvature. At the end of the main section, the channel width expands to 2000 μm before the filter captures the particles.

To confirm the flow resistances of the channels, a syringe pump (KD Scientific, Holliston) was used to push air into one inlet and on through the main section of the channels at a known flow rate Q, while the pressures at the inlet and at the node of the channel were measured with pressure sensors (ASDX Series 0 to 1 PSI and 0 to 15 PSI ranges, Honeywell International Inc.). Tests were done with flow rates between 100 μL/min and 1500 μL/min and resulted in flow resistances $$\begin{cases} R_{shroud} = \dfrac{P_{shroudport} - P_C}{Q} \\ R_{sample} = \dfrac{P_{sampleport} - P_C}{Q} \\ R_{outlet} = \dfrac{P_C}{Q} \end{cases} \quad (11)$$

with Q the flow rate set by the syringe pump.

B. Aerosol Generation and Flow Control

Aqueous suspensions of fluorescent-dyed carboxyl-functionalized monodisperse polystyrene latex (PSL) microspheres were used as test samples. The various sizes of PSL have different dyes, allowing them to be distinguished with a fluorescence microscope with the appropriate optical filters. Mixtures of differently-dyed sizes were aerosolized with an air jet nebulizer (Lovelace Nebulizer, InTox products; run at 15-25 PSI) and the resulting airstream was dried as it flowed through a tube containing desiccant. The amount of air entering the microchannel from the airstream was controlled by a valve connected to a bleed air line at the outlet of the nebulizer. The pressure at the split was measured and displayed in real time (LabView v. 8.5; National Instruments).

Pressure-controlled shroud air was provided by a MFCS-8C microfluidic pressure control system (Fluigent) with a range of 0-1000 mbar and a resolution of 0.3 mbar. For these and the following curved channel tests, each test was allowed to run for between 25 and 120 minutes (depending on the flow rates and particle concentrations), and then the filter paper was removed and imaged with the microscope.

C. Particle Detector

A prototype particle detector was assembled separately from the microchannel. Three particle sizes (0.75 μm, 2.28 μm, and 2.88 μm diameter) are each prepared at three different concentrations (0.1%, 0.01%, and 0.001% w/v). The output of the aerosol generator was sent through a sealed tube containing a filter (PallFlex E70-2075W, Pall Corporation), an LED (LTL1CHTBK2, Lite-On Inc.) upstream of the filter, and a photodiode (BS500A, Sharp Microelectronics) downstream of the filter. The signal from the photodiode was amplified and read into a PC with a data acquisition card (USB-6212, National Instruments).

Results

A. Straight Channels

The flow focusing and our model for cross-stream diffusion of the particles were validated in the straight channels. Tests were primarily performed with 0.75 μm particles, at a variety of ratios of shroud to sample air and velocities chosen within the range of conditions expected to be used for separation experiments. Images of the collected particles on the filter are taken with a fluorescence microscope and imported into MATLAB™ (v. R2009a, The MathWorks Inc.) as matrices representing the brightness of each pixel. The image brightness was summed along each column, resulting in a two-dimensional graph of the intensity of particles as a function of the position along the width of the outlet. FIG. 5 shows an example of such a graph. In FIG. 5, includes curves for the expected (with and without diffusion) and measured particle concentration along the channel width. The measured plot is an average of three tests taken under identical conditions: 0.21 µm diameter particles, with a total flow rate of 6.9 µL/s and a ratio of shroud to sample flow rates of 1:1.

Figure 6:
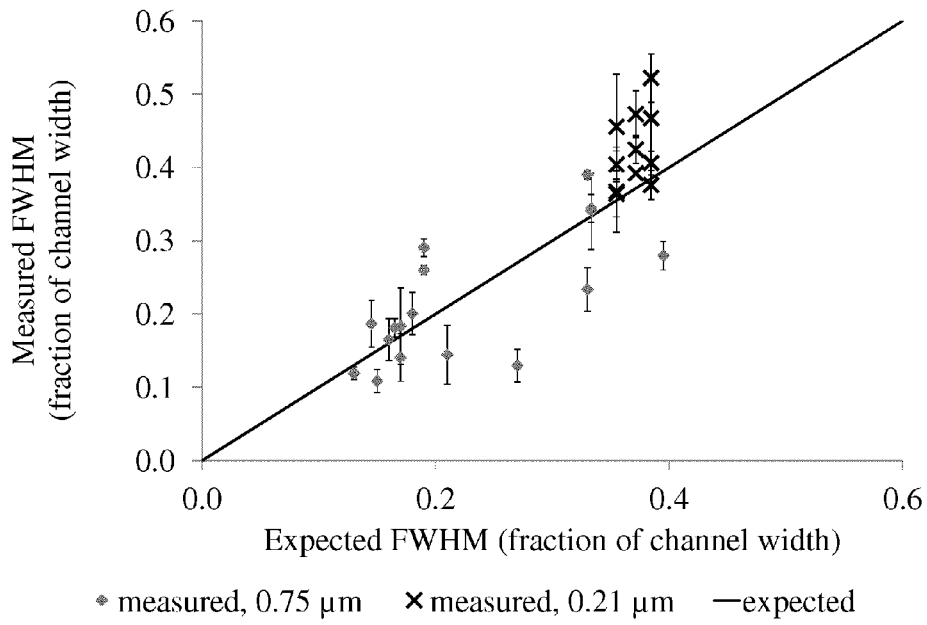
FIG. 6 is a graph showing the measured and expected widths of distributions of particles.

FIG. 6 is a graph of the full-width half-maximum (FWHM) width of the plot. FIG. 6 shows both expected (solid line) and measured (points) FWHM widths for straight channel experiments. Particles were 0.75 µm diameter (solid diamonds) or 0.21 µm diameter (X's).

The results summarized in FIGS. 5 and 6 showed good correlation between the width expected from modeling and the width from the experiments.

B. Separation Tests

Separation tests were performed on particles of sizes 0.75 µm, 0.97 µm, 2.28 µm, and 2.88 µm. The latter two sizes were chosen to correspond to a PM2.5 standard. Due to the limited availability of dyes that correspond to available filters, only two sizes of particles were separated at a time (Table 1). As in the straight channel experiments, images of the particles collected on the filter were analyzed with MATLAB.

TABLE I

MIXTURES OF PARTICLES USED FOR SEPARATION.

| Mixture | Particle 1 | Particle 2 |
|---------|------------|------------|
| 1 | 0.75 µm | 0.97 µm |
| 2 | 0.97 µm | 2.28 µm |
| 3 | 2.28 µm | 2.88 µm |

Figure 7:
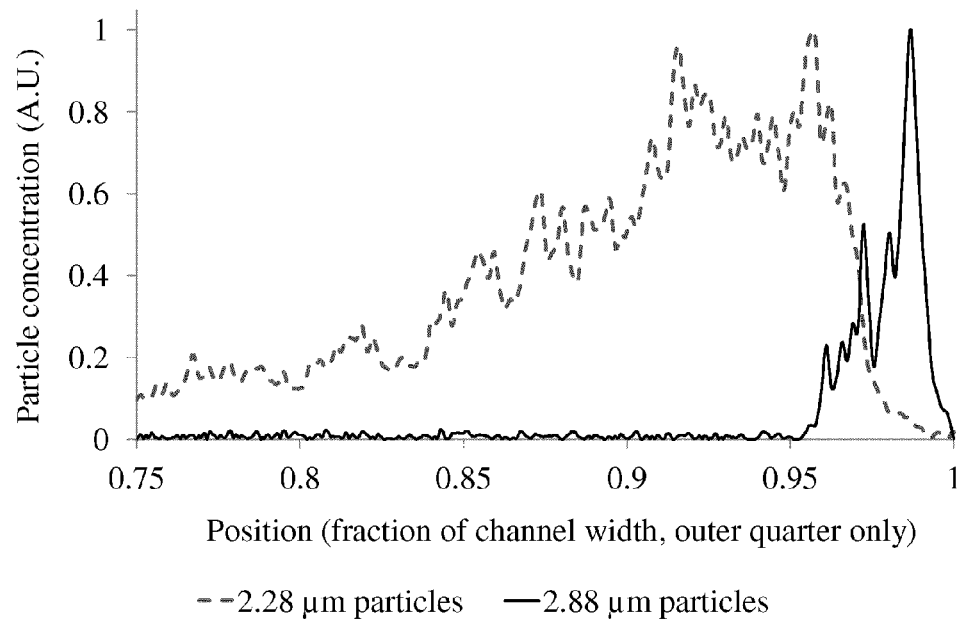
FIG. 7 is a graph showing the concentrations of particles of different sizes as a function of position.

The microscope's optical filters were used to obtain two different images, each showing only one of the two sizes of particles being separated, from which two corresponding plots of intensity were obtained. The centroid of each of the two plots was found to identify the mean difference in position of the two particle sizes. This is shown in FIG. 7 which shows the location of 2.28 µm and 2.88 µm particles after separation at an average velocity of 0.55 m/s; the plot shows only the radially outer quarter of the filter.

The pressure ranges used for separation experiments were 10-200 mbar (shroud) and 5-100 mbar (sample air).

Figure 8:
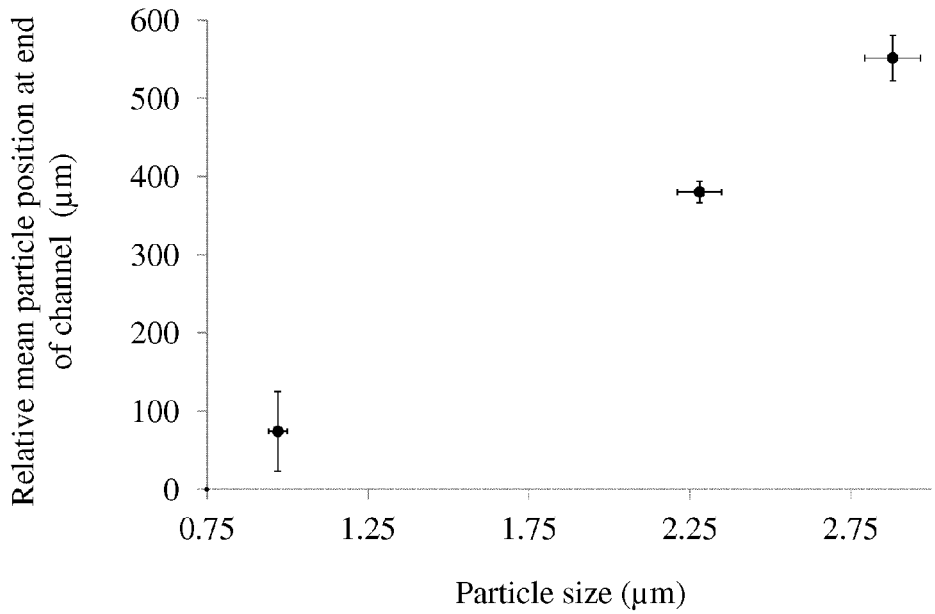
FIG. 8 is a graph showing relative mean particle position as a function of particle size.

The results showed a clear difference in the mean position of the larger two particle sizes from each other and from the smaller particles. FIG. 8 shows measured mean location of particles after separation, relative to that of 0.75 µm particles under identical conditions. The position of each particle size was measured relative to that of 0.75 µm diameter particles, because of the difficulties in precisely identifying the location of the channel outlet on the image of the filter after each test. Data is from several tests, average velocity 0.49 m/s.

The mean positions of the 2.28 µm particles and the 2.88 µm particles relative to the 0.75 µm particles were 19% and 28% of the full width of the channel outlet respectively. The mean position of the 0.97 µm particles relative to that of the 0.75 µm particles was only about 4% of the full width of the channel outlet. This small difference was as expected for these particles, because of their small size, and small size difference. Modeling of the particle separation predicts an achievable resolution of 0.5 µm with 80% accuracy (i.e., the regions of particles with that difference in size will overlap by less than 20%) for particle sizes in the 2-3 µm range.

The prototype apparatus can be tuned to separate particles of different sizes by adjusting the flow rate. For example, for particle diameters greater than approximately 2 µm, a flow velocity of about 0.25 m/s averaged over the channel cross-section is useful. For smaller particles, greater flow rates up to average flow velocities of 2 m/s or so may be used. The particular flow rates for achieving optimal separation of particles in a specific size range will depend upon the details of construction of the apparatus.

Figure 10:
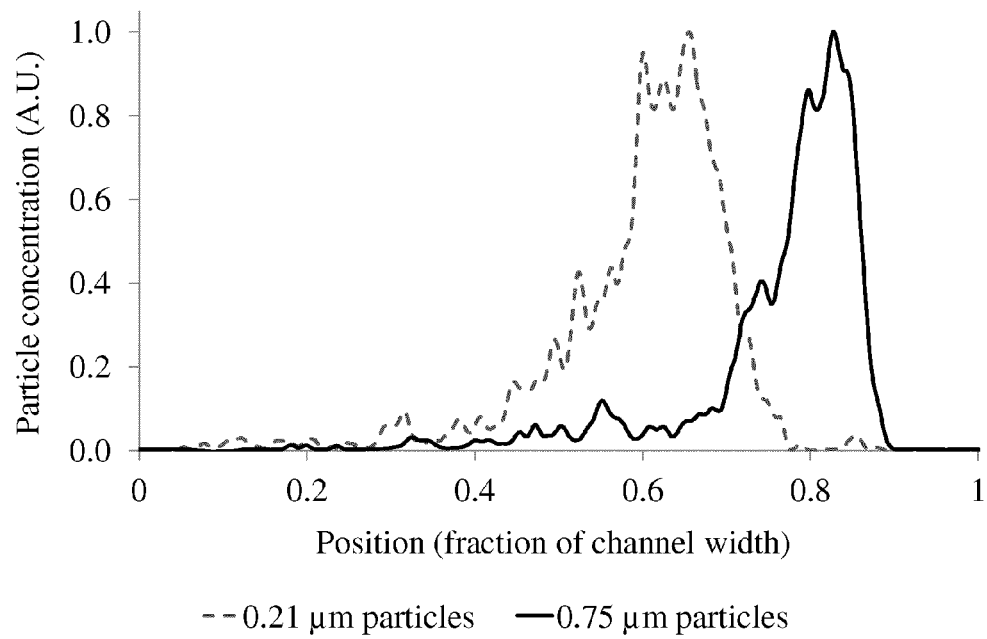
FIG. 10 is a graph showing the concentrations of particles of different sizes as a function of position.

A further experiment was conducted using the same prototype using a mixture of 0.21 µm and 0.75 µm particles, with mean channel velocity of 1.5 m/s and a shroud air to sample air ratio of 3:1 by volume. The results of this experiment are shown in FIG. 10, which shows concentrations of the different sized particles at positions along the radially outer quarter of the filter.

C. Particle Detection

Figure 9:
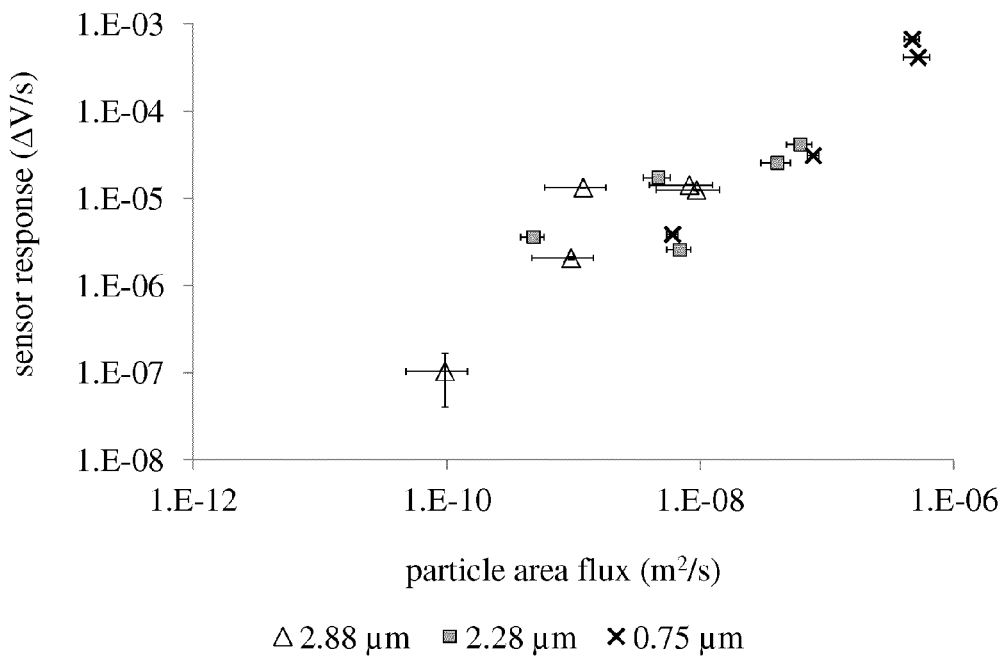
FIG. 9 is a graph showing sensor response as a function of particle area flux for particles of different sizes.

The change in the sensor signal was compared to the particles used in the test. The particle area flux was found by dividing the particle number concentration in air by the flow rate of the air and multiplying by the cross-sectional area per particle. The sensor responded well over four orders of magnitude of particle concentration over time periods ranging from a few minutes for the high concentrations to two hours for the low concentrations. FIG. 9 is a graph of detector response for particles of different diameters as indicated on the legend. "Particle area flux" is the product of particle flow rate and projected particle area.

Additional Embodiments

The principles described herein may be exploited in a wide range of additional embodiments. Such additional embodiments may combine one or more features of the apparatus and methods as described above with one or more additional features as described below.

Different embodiments may provide different mechanisms for detecting particles. Preferably the detection mechanisms permit position-sensitive detection of particles (i.e., preferred detection mechanism are configured to specifically detect particles one or more particular positions). In some embodiments, microchannel 22 comprises a widened section at a location after curved section 22 and one or more detectors are in the widened section.

Figure 11:
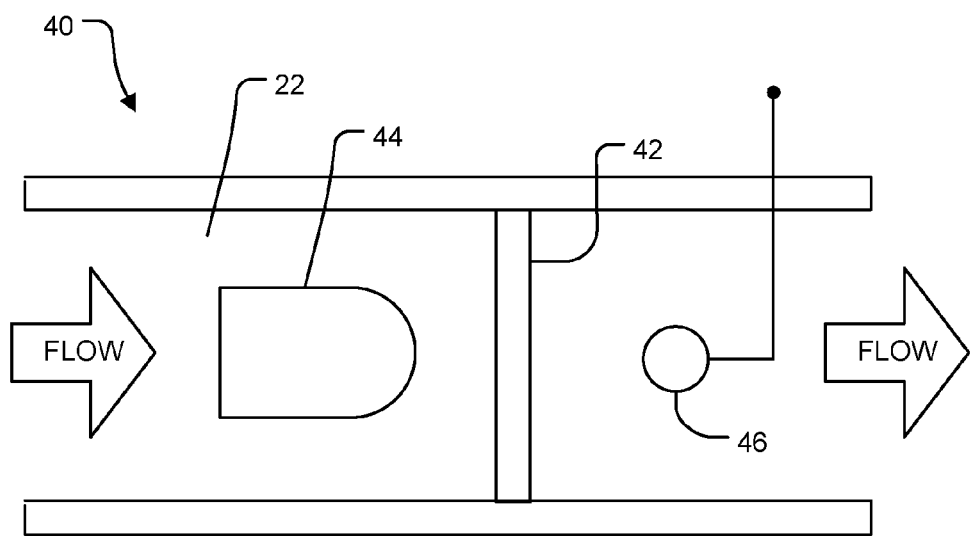
FIGS. 11 and 12 are schematic depictions of different particle detection arrangements.

FIG. 11 is a schematic diagram of a detector 40 according to an example embodiment. Detector 40 comprises a filter 42, a light emitter 44 and a light sensor 46. An air stream in which particles are entrained flows inside microchannel 22. Filter 42 collects particles entrained in the airstream. Light emitter 44 illuminates filter 42. Filter 42 is configured to pass at least some of the light from light emitter 44 to light sensor 46 (e.g., filter 42 may be at least partially translucent). Particles entrained in filter 44 may attenuate or block light from passing through filter 44 to light sensor 46. The presence of particles entrained in filter 44 may be estimated or inferred from the amount of light detected by light sensor 46. Light sensor 46 may, for example, comprise a CCD, phototransistor, photodiode or other suitable light sensor.

In some embodiments, detector 40 is configured to specifically detect particles in a particular transverse section of channel 22 by having sensor 46 receive only light transmitted by a specific transverse section of filter 42 (e.g., a specific transverse section of filter 42 at which particles of a particular size are collected). For example:

- light emitter 44 may configured to illuminate only the specific transverse section of filter 42;
- filter 42 may comprise opaque and translucent transverse sections, with the translucent section corresponding in location to the specific transverse section;
- light sensor 46 may be configured to receive only light passed by the specific transverse section of filter 42 (e.g., light sensor 46 may be placed in contact with or closely adjacent the specific transverse section of filter 42, a light guide may channel light from the specific transverse section of filter 42 to light sensor 46, etc.);

In each of the above examples, only particles collected in the specific transverse section of filter 42 affect the amount of light reaching light sensor 46.

In some embodiments, detector 40 is configured to separately detect particles at a plurality of different transverse sections of microchannel 22. For example, detector 40 may comprise a plurality of light sensors 46 that each correspond to a different specific transverse section of filter 42. For another example, detector 40 may comprise a plurality of light emitters 44, each configured to illuminate a different transverse section of filter 42. In this example, the plurality of light emitters may be turned on separately in sequence, such that only one of the corresponding transverse sections of filter 42 is illuminated at a time. The output of light sensor 46 may be provided to logic circuitry that associates detected light with the particular transverse section of filter 44 illuminated at the time the light was detected.

In some embodiments, a particle detector provides real-time particle detection by sensing energy (e.g., light) scattered by particles moving through a beam of energy. Pulses of scattered energy caused by moving particles may be counted over time, and a concentration of the particles derived from the count, the time period and the flow rate of sample fluid into the apparatus. In some embodiments, the intensity of scattered energy registered by a sensor (e.g., as indicated by a voltage level output by the sensor) is averaged over a moving window, and the average value is correlated to a concentration of particles based on the flow rate of the sample fluid into the apparatus, the intensity of energy emitted into the channel and the pre-determined intensity of scattered energy returned by various concentrations of particles in the channel (such as may be computed analytically, determined from simulations, or determined from experiments).

Figure 12:
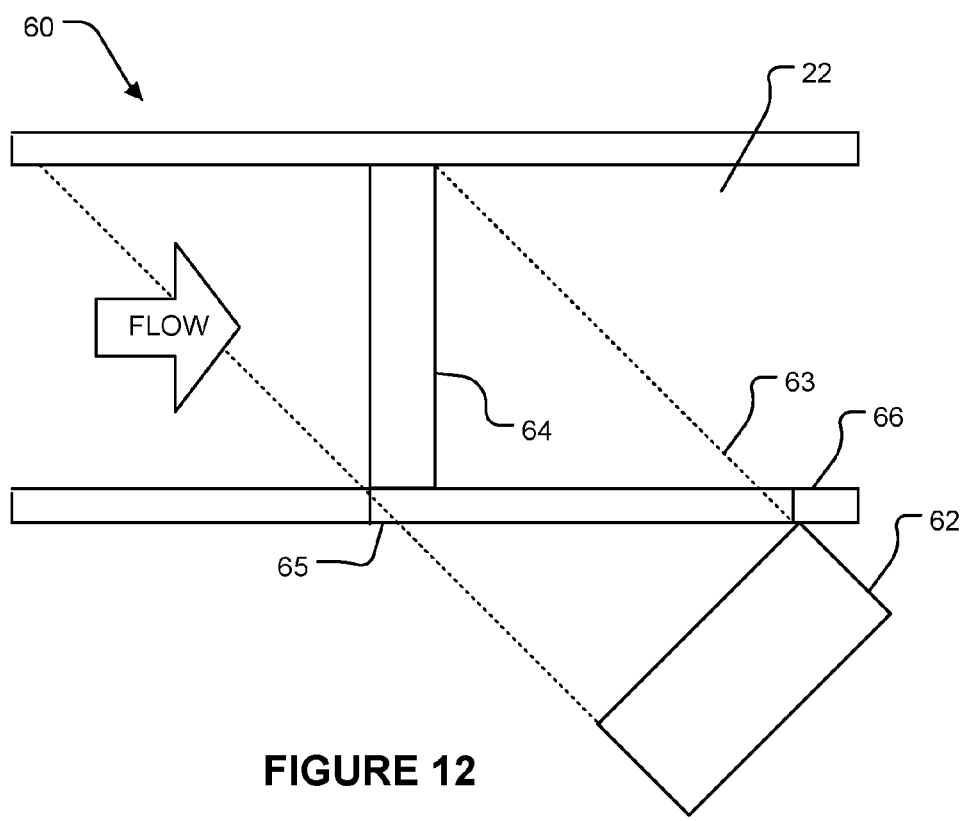

FIG. 12 is a schematic diagram of a real-time particle detector 60 according to another example embodiment. Detector 60 comprises a light source 62 and a light sensor 64. Light source 62 is configured to emit a beam of light 63 into microchannel 22 through a transparent portion 65 of the wall 66 that defines one side of channel 22. In the illustrated embodiment, beam of light 63 is directed into the flow of fluid in channel 22 at an angle. Beam of light 63 is generally parallel to the plane of light sensor 64. It is preferable that beam of light 63 be closely spaced to the plane of light sensor 64 (e.g., by a distance of less than 1 mm). Light scattered from beam 63 traveling in channel 22 is detected by light sensor 64.

Figure 13:
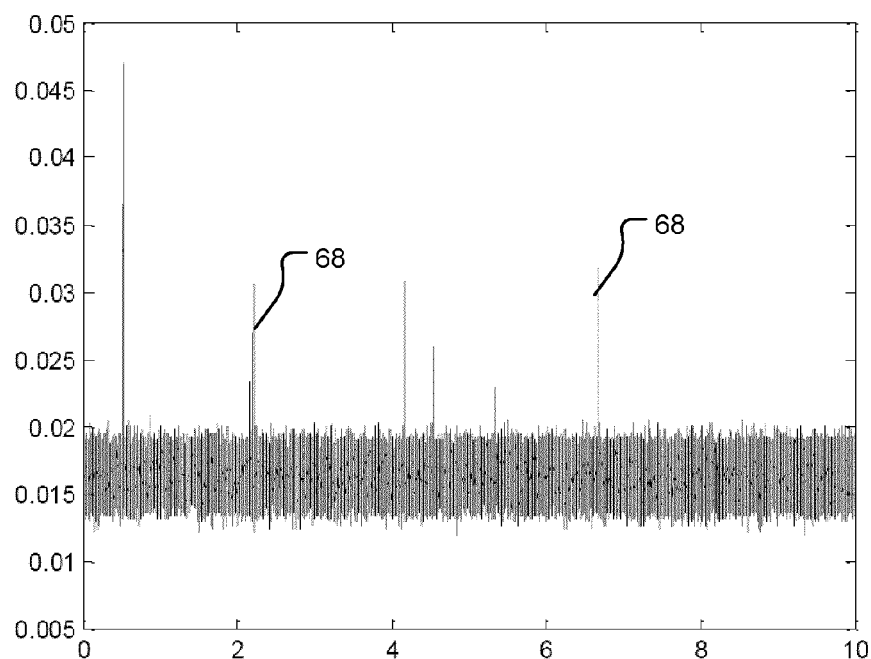
FIG. 13 is a graph showing output of light sensor in an example particle detection arrangement.

Signals output by light sensor 64 may be filtered to improve particle detection, reject noise and/or the like. FIG. 13 shows a plot of experimental data obtained using a prototype detector. The data plotted in FIG. 13 is a moving window average of the voltage signal output by the light sensor of the prototype detector over time. Pulses 68 in the data correspond to occurrences of particles scattering light as they pass through the detector's light beam. Pulses 68 may be counted (e.g., by logic circuitry coupled to receive the output of sensor 64) and used to determine a concentration of the particles.

In some embodiments, a detector comprises a plurality of light sources (e.g., opposed light sensors on opposite sides of channel 22). The outputs of such plural light sources may be combined (e.g., summed, logical OR, logical AND, etc.) to improve particle detection, provide noise rejection, or the like.

In some embodiments, beam of light 63 is oriented across channel 22, such that particles passing sensor 64 in any part of channel 22 will scatter light from beam 63 to sensor 64.

In other embodiments, beam of light 63 is arranged to illuminate only a specific transverse section of channel 22 (such as with a collimated beam, coherent beam, or the like, for example). In these embodiments, only particles passing sensor 64 in the illuminated transverse section of channel 22 will scatter light from beam 63 to sensor 64.

Figure 14:
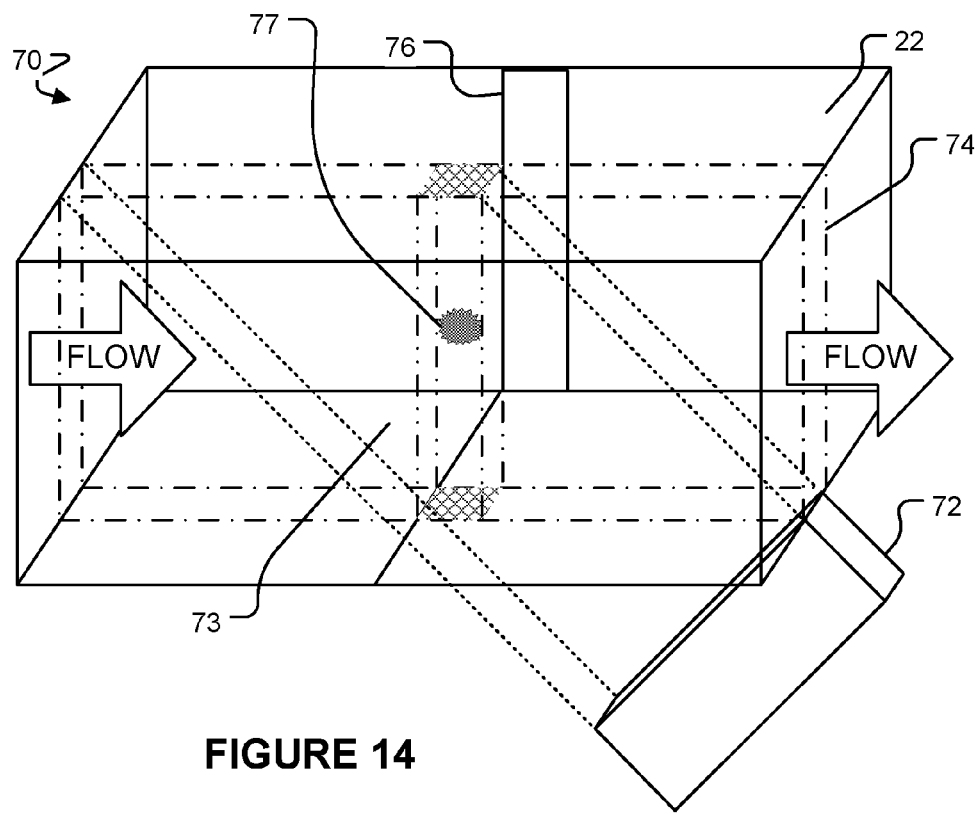
FIGS. 14 and 15 are schematic depictions of different particle detection arrangements.

FIG. 14 is a perspective schematic illustration of an example real-time particle detector 70 in which a light source 72 is configured to illuminate only a specific transverse section 74 of channel 22. In detector 70, light source 72 projects a beam of light 73 that illuminates transverse section 74 of channel 22. Light sensor 76 detects light scattered by a particle 77 traveling in transverse section 74 when it passes through beam 73. In some embodiments, light source 72 is movable across channel 22 to selectively illuminate different transverse sections of channel 22. Detected instances of scattered light may be correlated with the transverse section illuminated at the time of detection, and in this manner particles traveling in a plurality of different transverse sections of channel 22 can be counted separately.

In some embodiments, detector 70 comprises a plurality of light sources that each illuminate different transverse sections of channel 22. Light sources in such embodiments may be cycled to illuminate their respective transverse sections of channel 22 in turn. The cycling period for each light source may be matched to the time it takes for a particle traveling in channel 22 to pass through the beam of light, for example.

Figure 15:
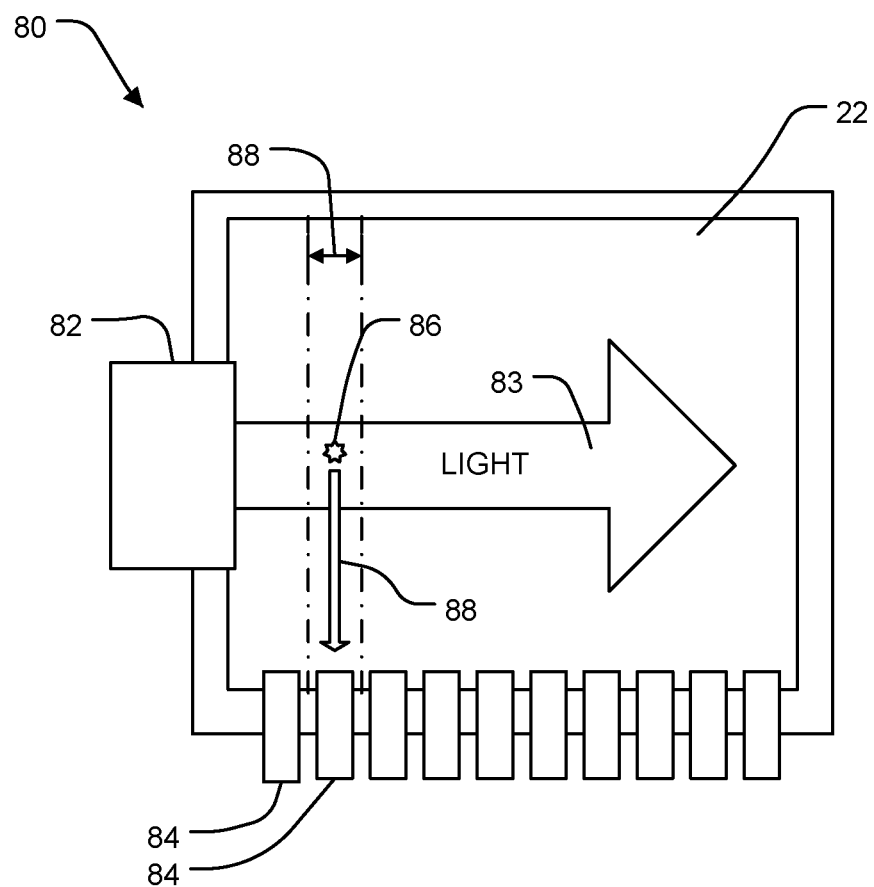

FIG. 15 illustrates another example real-time particle detector 80. Detector 80 comprises a light source 82 configured to emit a beam of light 83 into microchannel 22. Beam of light 83 may be generally parallel to the plane of curved section 25. One or more light sensors 84 are provided. Scattered light 85 from a particle 86 in a particular transverse section 88 of microchannel 22 is detected by a corresponding sensor 84. Light sensors 84 detect light coming from directly above and so particles at different positions across microchannel 22 are counted by different sensors 84.

Detectors described herein may comprise optical apparatus, such as reflectors, light guides and the like, for example, that direct scattered light to the appropriate sensors. Other suitable particle detection technologies may also be used to detect particles that have been sorted by size as described herein.

In some embodiments, fluid flow is divided into a plurality of streams by a divider. A divider may be located to divide the flow at a location such that larger particles will travel down one sub-channel and smaller particles down another sub-channel. Particle detectors may be provided to register the presence of particles in one or more of the sub-channels.

Figure 16:
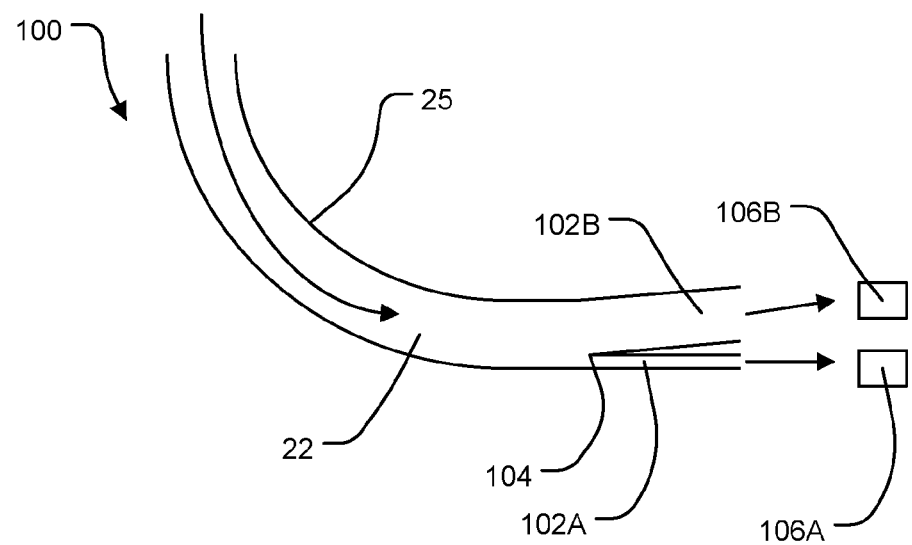
FIGS. 16 and 17 are schematic depictions of example embodiments that include sub-channel dividers.

FIG. 16 shows a portion of apparatus 100 which includes the final part of curved section 25 of a microchannel 22. Microchannel 22 is split into sub-channels 102A and 102B by a divider 104. Divider 104 is generally parallel to the axis of the curvature of curved section 25 (e.g., into the page of FIG. 11). In the illustrated embodiment, divider 104 comprises a sharp edge to encourage clean separation of the gas flowing in different transverse sections of microchannel 22 into separate flows in subchannels 106A and 106B. Particle detectors 106A and 106B are provided downstream in sub-channels 102A and 102B respectively. With particles separated by size into different sub-channels, any suitable particle detection technologies may be provided for one or more of the sub-channels to permit size-specific measuring of particle concentration.

The transverse location of divider 104 in microchannel 22 may be selected so that, for a given flow rate in microchannel 22 particles of a desired size range are separated into sub-channel 102A for counting by detector 106A. Some embodiments comprise a plurality of dividers configured to separate gas flowing in microchannel 22 into three or more sub-channels.

In the embodiment shown in FIG. 1, microchannel 22 turns through 180 degrees in curved section 25. This is not mandatory, Microchannel 22 could turn through more or less than 180 degrees in curved section 25. In some embodiments microchannel 22 turns through at least 90 degrees in curved section 25.

A smaller angle (for example 90 degrees to 120 degrees) would improve performance for separating larger particles (for example particles having sizes of 1-5 microns). To achieve separation of such particles with a curved section that turns through a reduced angle would require higher flow velocities/pressures to achieve the same separation as could be achieved using a curved section that turns through a greater angle. However, higher flow rates can be advantageous because such higher flow rates and pressures can be easier to control with a desired degree of accuracy than lower flow rates and pressures. A reduced angle of turn will, however, decrease the ability to separate very small (e.g. sub-micron) particles. The velocities required to separate sub-micron particles with a reduced angle of turn could be so high in some cases as to create secondary (Dean) flows. In general, it is desirable to maintain flow velocities small enough so as to maintain laminar flow conditions and to avoid secondary flows within microchannel 22.

Figure 17:
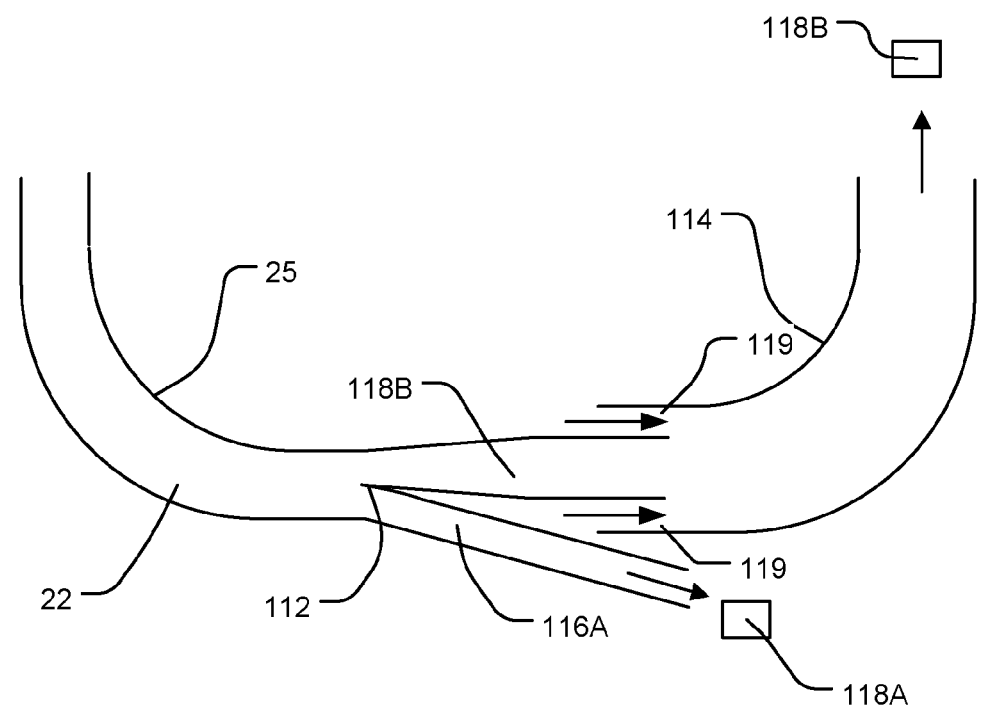

In some embodiments, fluid flowing in a sub-channel may be passed though a second curved section. FIG. 17 shows a portion of apparatus 110 which includes the final part of curved section 25 of a microchannel 22, a divider 112 and a second curved section 114 downstream from divider 112. Divider 112 splits channel 22 into sub-channels 116A and 116B. In operation of apparatus 110, larger particles, which tend to move outwardly more than smaller particles as they pass through curved section 25, are diverted into sub-channel 116A. Particle detector 118A is provided downstream in subchannel 116A.

Sub-channel 116B widens downstream from divider 112, which reduces the velocity of fluid (and particles entrained therein) flowing into sub-channel 118B from channel 22. Further downstream but upstream of second curved section 114, this fluid is sandwiched between shroud fluid introduced along the sides of sub-channel 118B via shroud ports 119. Particles diverted into sub-channel 118B at divider 112 are again exposed to centrifugal forces when they pass through second curved section 114. The reduction in velocity effected by the widening of sub-channel 118B upstream of second curved section 114 may help to avoid secondary flows (e.g., Dean flows) in second curved section 114. A particle detector 118B is provided downstream of second curved section 114.

Under laminar flow conditions, fluid flowing near the walls of a channel will generally have lower velocity than fluid flowing in the center of the channel. As a result, when particles entrained in the fluid pass through a curved section of the channel, particles near the center of the channel, which have relatively higher velocity, experience relatively higher centrifugal forces than the particles near the walls of the channel. This may negatively affect particle size separation, such as where larger particles traveling near a wall parallel to the plane of curvature of a curved section experience the same centrifugal force as smaller particles having the same transverse alignment and traveling in the vertical center of the channel.

A divider may divide the flow at a location downstream from curved section 25 to separate fluid flow of relatively higher velocity (e.g., air flow near the center of microchannel 22) from fluid flow having relatively lower velocity (e.g., air flow near the edges of microchannel 22). Where the fluid flow of relatively higher velocity is supplied to a detector, particle separation resolution may be improved (e.g., by excluding lower velocity particles from a sub-channel leading to a particle detector). This may be achieved, for example, by dividing the channel into top, middle and bottom sub-channels downstream from the curved section. Particles traveling the middle sub-channel will have more uniform velocity, and better particle size discrimination.

In some embodiments, flows of shroud gas are also introduced from sides of microchannel 22 above and/or below the plane of the substrate in which microchannel 22 is formed (e.g., walls between the walls that lead to the inside and outside of curved section 25). Such embodiments are advantageous as the flowing shroud gas keeps the test air and its entrained particles out of the slowest-flowing boundary regions adjacent the walls of microchannel 22. This tends to reduce the spread of flow velocities of particles carried in the test air entering curved section 25. This in turn facilitates improved particle size discrimination.

Another way to cause the test air to be entrained in the middle of a flow of shroud gas away from walls of microchannel 22 is to start with a clean stream of shroud gas flowing in microchannel 22 and to inject the air to be tested through a sample fluid introduction port along the bottom (or top) wall in the transverse centre of the channel. Downstream, more shroud air is injected from the bottom (or top) in order to carry the sample stream off the bottom (or top) wall.

In some embodiments where shroud gas surrounds a flow of test air in the middle of the channel, the ratio of shroud gas flow to test air flow downstream from junction 34 is one of at least 25:1, at least 50:1 and at least 100:1.

Figure 18:
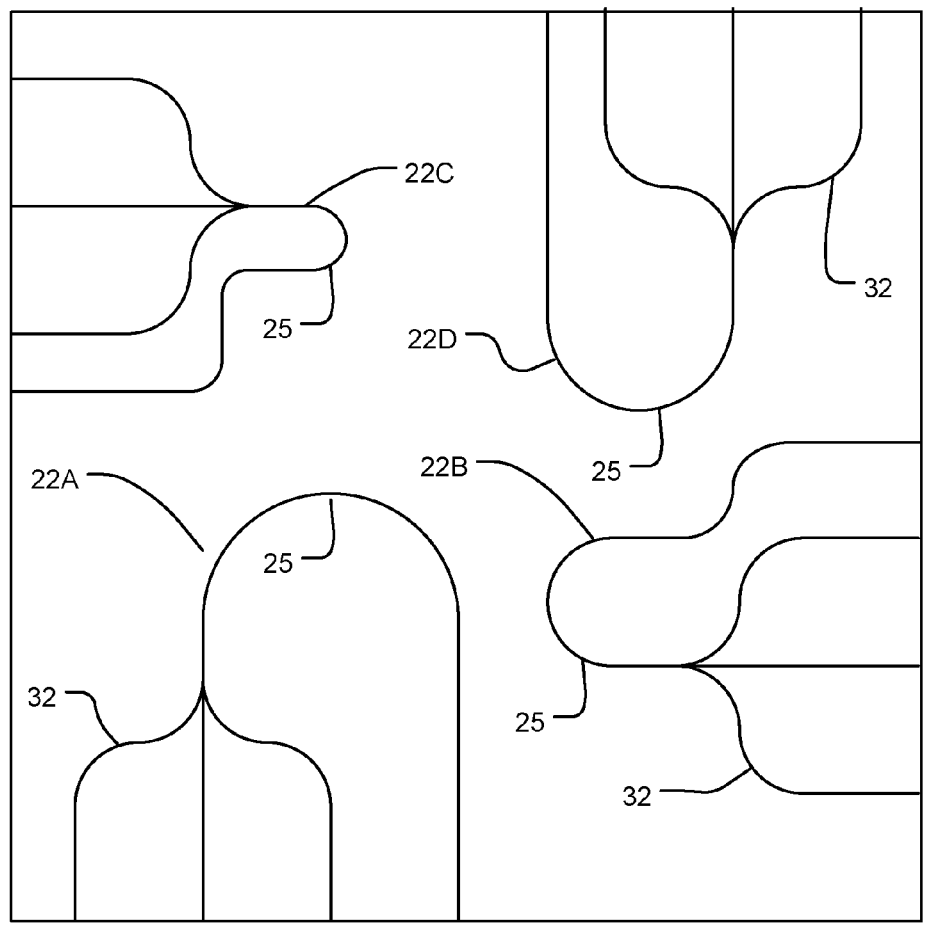
FIG. 18 is a schematic depiction of a substrate having formed on it microchannels with curved sections having various different radius of curvature.

Apparatus according to some embodiments comprise a plurality of different microchannels having a plurality of different curvatures. Different ones of the microchannels may be used to sense airborne particles of different sizes. This is illustrated schematically in FIG. 18 which shows a substrate 70 having formed on it microchannels 22A, 22B, 22C and 22D each having a curved section 25 of a radius of curvature different from that of the other microchannels. Each of the microchannels has associated channels 32 for shroud gas. Suitable particle detectors (not shown) are associated with each of the microchannels. In some embodiments of the general type shown in FIG. 18, the same flow rate is maintained in each of microchannels 22.

Figure 19:
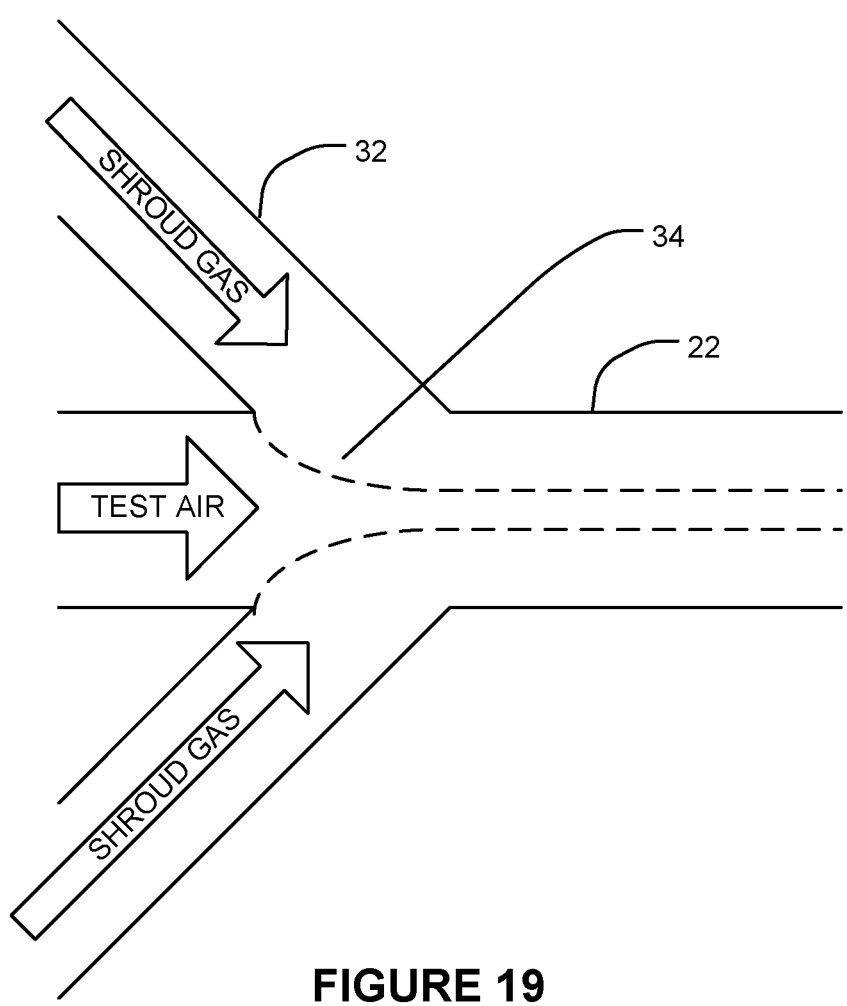
FIG. 19 illustrates sandwiching of a sample fluid stream between shroud fluid streams.

The introduction of shroud gas and/or sample fluid containing particles of interest may be varied. It is generally desirable that the gas containing entrained particles to be detected is confined to a stream that has a relatively small transverse dimension in microchannel 22. This is illustrated in FIG. 19 which shows schematically how flows of shroud gas entering from either side of microchannel 22 can focus the test air flow into a ribbon flowing along the center of microchannel 22 between streams of clean shroud gas. The transverse thickness of the ribbon of flowing test air will depend upon the ratio of air flow to shroud gas flow. Increasing the ratio of shroud gas flow to test air flow tends to reduce the thickness of the ribbon. In some embodiments the ratio of shroud gas flow to test air flow downstream from junction 34 is at least 5:1 or at least 10:1.

It is not mandatory that all shroud gas be introduced into microchannel 22 at a single junction point. Shroud gas could be added at points spaced apart along microchannel 22 upstream from curved section 25.

It is not mandatory that the shroud gas entering the different sides of microchannel 22 be entering at the same rate. In some embodiments shroud gas is introduced with a higher flow rate on the side of microchannel 22 that leads into the outside of curved section 25 and shroud gas is introduced with a lower flow rate on the side of microchannel 22 that leads into the inside of curved section 25. In such embodiments, the ribbon of flowing test air may enter curved section 25 off center in microchannel 22 toward the inside of the curve. This provides a greater thickness of shroud gas toward the outside of the curve into which particles may be urged by centrifugal forces. In some embodiments, shroud gas is only provided on the side of microchannel 22 leading to the outside (greater-radius side) of curved section 25.

Controlling the flow rates of shroud gas on the sides of microchannel 22 may be used to displace the ribbon of flowing test air into a specific transverse section of microchannel 22. In some embodiments, variable valves controllably introduce shroud gas that displaces the ribbon of test air to align a particular transverse section of the flowing test air (e.g., a section likely to contain particles of a particular pre-determined size) with a particular transverse section of microchannel 22 (e.g., a section monitored by a particle detector, a section corresponding to a particular sub-channel, etc.). Shroud gas may be introduced upstream and/or downstream of curved section 25 to displace the flowing test air in this manner. In some embodiments, total flow rates and/or shroud flow rates can be varied dynamically to allow sampling of different particles sizes in the detector region and resolution of different size ranges of particles on the fly.

Some embodiments comprise control systems that provide active control over gas flow rates. Such embodiments may, for example, comprise flow sensors and/or gas pressure sensors located to monitor gas flow in microchannel 22 and/or shroud air channels 32. In some embodiments the flow sensors comprise miniature (in some embodiments micromachined) mass flow sensors such as calorimetric or micromechanical) sensors. Signals from the flow sensors may be provided to a controller that controls flow in the microchannels by opening or closing variable valves. The variable valves may be external to substrate 20 or may be formed in substrate 20 for example by suitable micromachining processes. The controller may comprise a commercially available process controller, for example.

Figure 20:
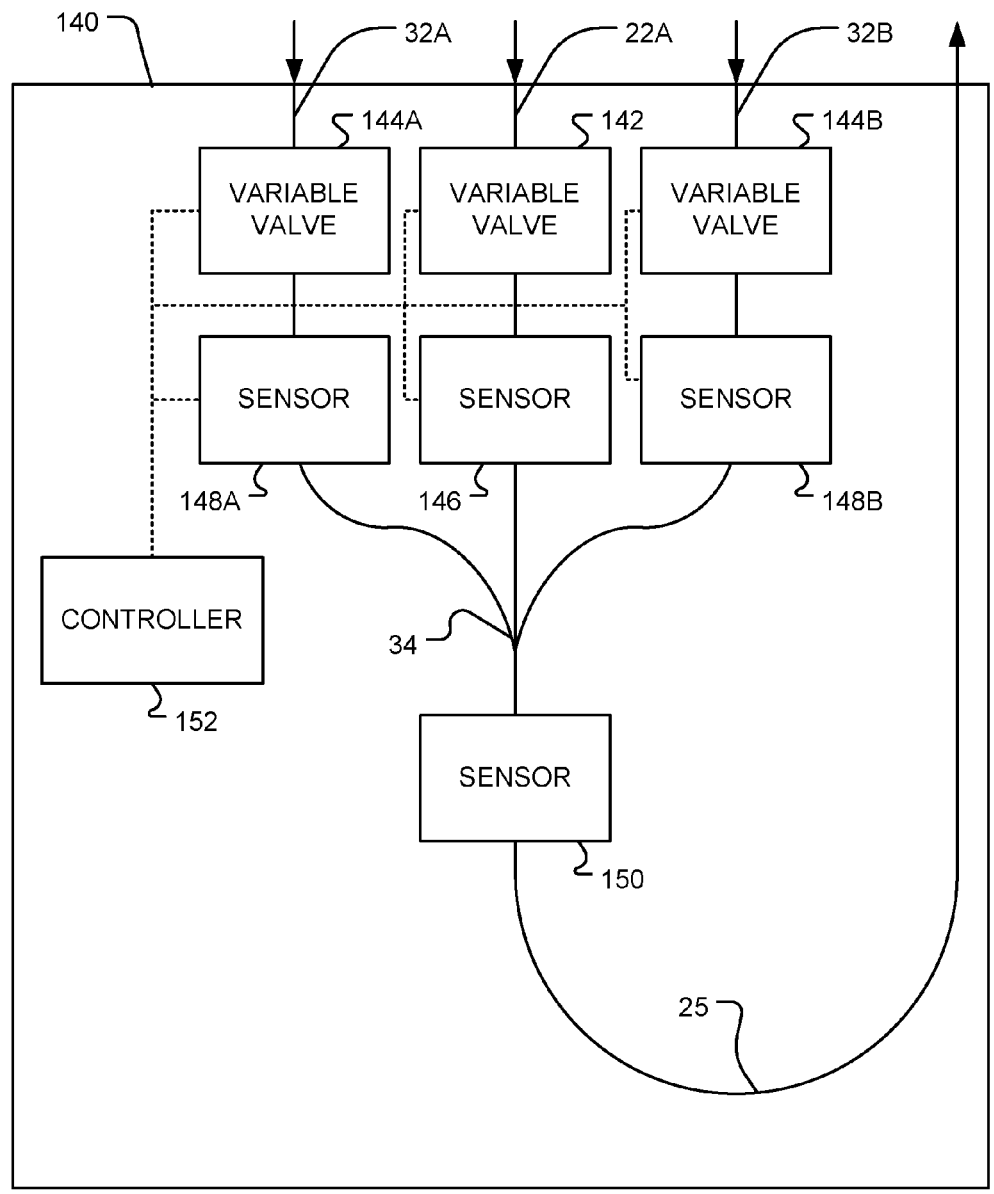
FIG. 20 is a schematic detection of a particle size separator according to an example embodiment.

FIG. 20 shows a particle size selector 140 according to an example embodiment. Particle size selector 140 is generally similar to particle size selector 20, and like reference numerals are used to denote like features, which are not described again here. Particle size selector 140 comprises a variable valve 142 operable to control the flow of sample fluid into channel 22. More particularly, variable valve 142 is operable to control the flow of sample fluid introduced into channel 22 via sample fluid introduction port 22A.

Particle size selector 140 comprises variable valves 144A and 144B, which are operable to independently control flow of shroud fluid through outside shroud fluid port 32A and inside shroud fluid port 32B, respectively. Accordingly, variable shroud flow valves 144A and 144B are each operable to control flow of shroud fluid into channel 22. Variable valves 142, 144A and 144B may be controlled in conjunction to obtain a particular total flow rate in channel 22, and thereby obtain a particular fluid velocity in channel 22. Variable valves 142, 144A and 144B may also be controlled in conjunction to obtain a particular ratio of shroud flow to sample fluid flow. By controlling variable shroud flow valves 144A and 144B, the relative flows of shroud fluid on the outside and inside of curved section 25 may be adjusted to steer the flow of sample fluid across channel 22.

Particle size selector 140 comprises sensors 146, 148A and 148B operable to detect at least one of a flow rate and a pressure of fluid flow controlled by variable valves 142, 144A and 144B, respectively. Particle size sensor 140 also comprises sensor 150, which is operable to detect at least one of a flow rate and a pressure of fluid in channel 22 downstream of junction 34 and upstream of curved section 25.

Particle size selector 140 comprises a controller 152 communicatively coupled to variable valves 142, 144A and 144B and to sensors 146, 148A, 148B and 150. Controller 152 may comprise one or more central processing units (CPUs), one or more microprocessors, one or more field programmable gate arrays (FPGAs), application specific integrated circuits, logic circuits, or any combination thereof, or any other suitable processing unit(s) comprising hardware and/or software capable of functioning as described herein. Controller 152 may be configured to control one or more of variable valves 142, 144A and 144B to maintain laminar flow conditions in channel 22 based at least in part on the at least one of the flow rate and the pressure detected by sensor 150. Controller may be configured to control one or more of variable valves 142, 144A and 144B based the at least one of the flow rate and the pressure detected by sensors 146, 148A, 148B and/or 150 (e.g., to achieve a desired ratio of shroud fluid to sample fluid in channel 22, to steer a ribbon to sample fluid to a particular transverse section of channel 22, etc.). In some embodiments, variable shroud flow valves controllable by controller 152 are provided downstream of curved section 25.

Figure 21A:
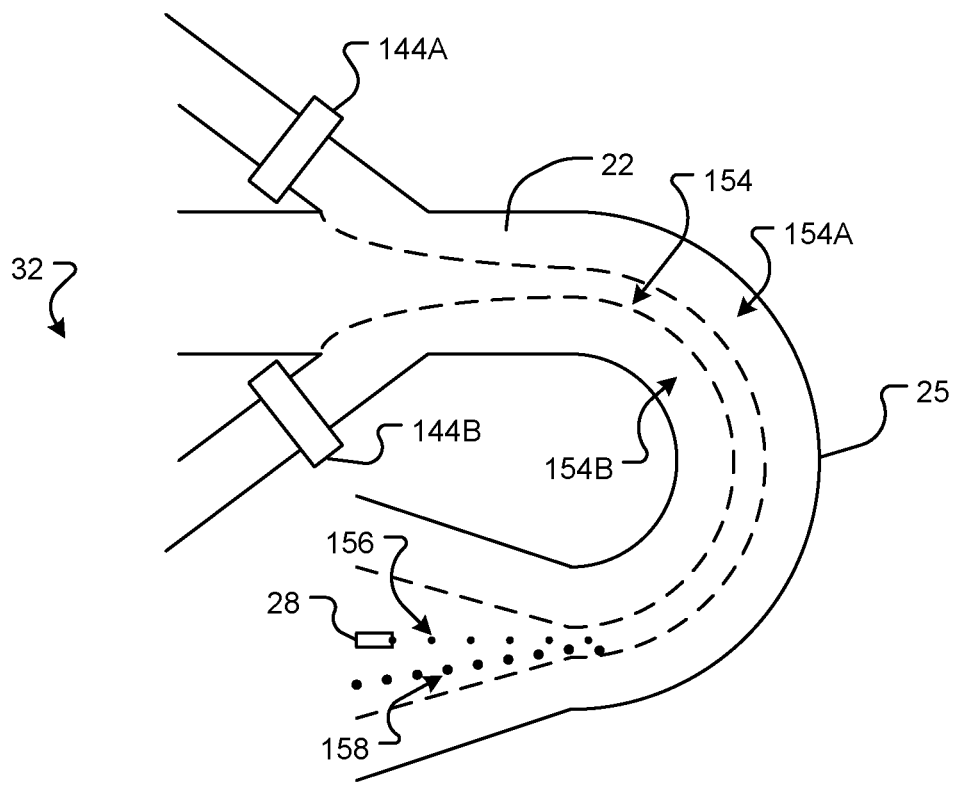
FIGS. 21A and 21B are schematic illustrations of use of the particle size separator shown in FIG. 20 in detecting differently sized particles.
Figure 21B:
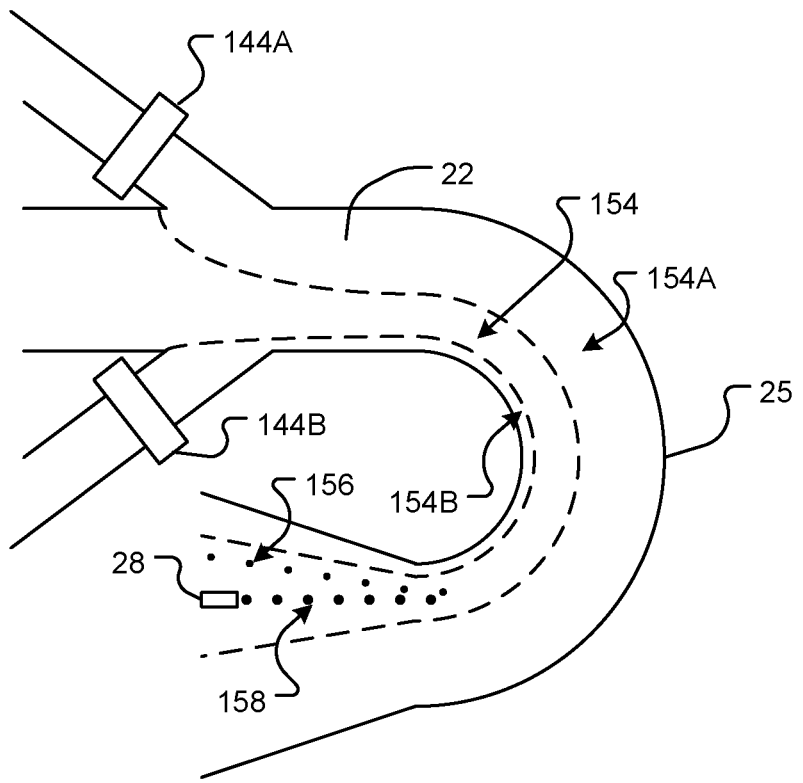

FIGS. 21A and 21B show an example use of particle size selector 140 to steer different transverse sections of a sample air stream 154 to the particular transverse section of channel 22 where sensor 28 is located. In FIG. 21A, variable shroud flow valves 144A and 144B supply shroud gas to channel 22 at the same rate. As a result, sample air flow 154 is sandwiched between shroud flows 154A and 154B in approximately the middle of channel 22. Passage of sample air flow 154 through curved section 25 separates particles of two different sizes in sample air flow 154 into different transverse sections of sample air flow 154. Smaller particles 156 are aligned with a transverse section of channel 22 at which sensor 28 is positioned. As a result, smaller particles 156 are detected by sensor 28. Larger particles 158 are aligned with a transverse section of channel 22 that is outward of sensor 28, and are not detected by sensor 28.

In FIG. 21B, variable shroud flow valve 144A supplies shroud gas to channel 22 at a greater flow rate than variable shroud flow valve 144B. As a result, sample air flow 154 is sandwiched between shroud flows 154A and 154B to the inside of the middle of channel 22. As a result, particles 156 and 158 are displaced toward the inside of channel 22. The displacement effected by the relative increase of outside shroud flow 154A causes larger particles 158 to be aligned with the transverse section of channel 22 at which sensor 28 is positioned. As a result, larger particles 158 are detected by sensor 28. Smaller particles 156 are aligned with a transverse section of channel 22 that is inward of sensor 28, and are not detected by sensor 28.

In some embodiments a particle detector apparatus comprises first and second substrates. Microchannels 22, 32 are formed in one substrate and components for flow sensors, particle sensors, pressure sensors and/or flow control valves are formed on a face of another substrate that closes microchannels 22, 32. This is illustrated schematically in FIG. 22 which shows one substrate 163 in which microchannels 22 and 32 are formed and another substrate 164 carrying components 165 for various sensors. When substrates 163 and 164 are held or bonded together microchannels 22, 32 are closed and sensor components 165 are aligned with corresponding locations in microchannels 22, 32. The sensor components may comprise, for example, light sources, light detectors, calorimetric flow sensors, pressure sensors or the like. Flow control valve components are also formed in substrate 64 in some embodiments.

In some embodiments microchannel 22 comprises a long narrow sample inlet or other flow restriction upstream from junction 34. This can facilitate control of the flow through microchannel 22 as it can be easier to maintain accurate control of somewhat higher pressures than to maintain accurate control over very low pressures.

Microchannel 22 may be made from any suitable material using any suitable manufacturing process. Some example materials include glass, silicon, metals, suitable polymers and the like. It is thought to be generally desirable that the substrate in which microchannel 22 is formed is not a good electrical insulator but instead conducts electricity at least somewhat so as to avoid the buildup of static electricity. Advantageously, microchannels suitable for application in at least some embodiments of the invention may be manufactured using inexpensive molding processes. In some embodiments, the microchannel walls are coated with a layer of metal or another electrically conducting coating.

Dimensions of microchannel 22 and shroud channels 32 are not critical and may be varied significantly. While the prototype had channels 100 μm high, with shroud inlets 40 μm wide and the main section of microchannel 22 60 μm wide, one could practise the invention with larger or smaller channel dimensions. Larger transverse dimensions have the advantage of providing more room for particles of different sizes to separate into (which can facilitate detection of particles of different sizes) and the disadvantage that the radius of curvature in curved section 25 and the overall size of the apparatus may need to be increased to maintain laminar flow conditions without secondary circulation (such as may be caused by turbulent flow and/or Dean vortices, for example). In some embodiments, microchannel 22 has transverse width upstream from curved section 25 in the range of 200 μm±140 μm the height of microchannel 22 may be in this same range. In some embodiments, microchannel 22 has transverse width upstream from curved section 25 less than 1 mm. In some embodiments, microchannel 22 has hydraulic diameter of at least 100 μm.

While the prototype had curved section 25 with radius of curvature of 5 mm, the invention may be practiced with different radii of curvature. Larger radii of curvature have the disadvantage of a larger footprint for the same curve angle and requiring larger flow velocities to obtain equivalent transverse dispersion of particles. An upper limit on the radius of curvature is imposed by this latter disadvantage because Dean vortices are prone to develop at higher flow velocities. By way of example, a radius of 5 cm with an angle around 25° in a 100 μm×100 μm channel operated with an air flow having velocity of 5 m/s to displace 1 μm particles by 10 μm (10% of the channel width) would have a Dean number greater than one. Conversely, very small radii of curvature (e.g., less than about 1 mm) may also lead to a high Dean number. In some embodiments, a curved section has radius of curvature that is one or both of greater than 1 mm and less than 5 cm. While it is convenient, it is not mandatory that the radius of curvature be constant throughout curved section 25.

Apparatus as described herein may be optimized for detecting particles in specific size ranges of interest by suitably selecting the radius of curvature in curved section 25, selecting an appropriate flow rate (corresponding to an appropriate flow velocity) and providing appropriate particle detectors. Depending on the implementation of the detection mechanism particles of different size ranges may be discriminated by dividing the flow so as to separate the particles with a flow divider or detecting particles at different locations across the channel using a suitable position-sensitive detector.

In some embodiments a particle detector is provided to detect particles at a location to which particles having sizes in the range of 0.2 to 3 μm are directed as a result of the flow of the test air around curved section 25.

Figure 22:
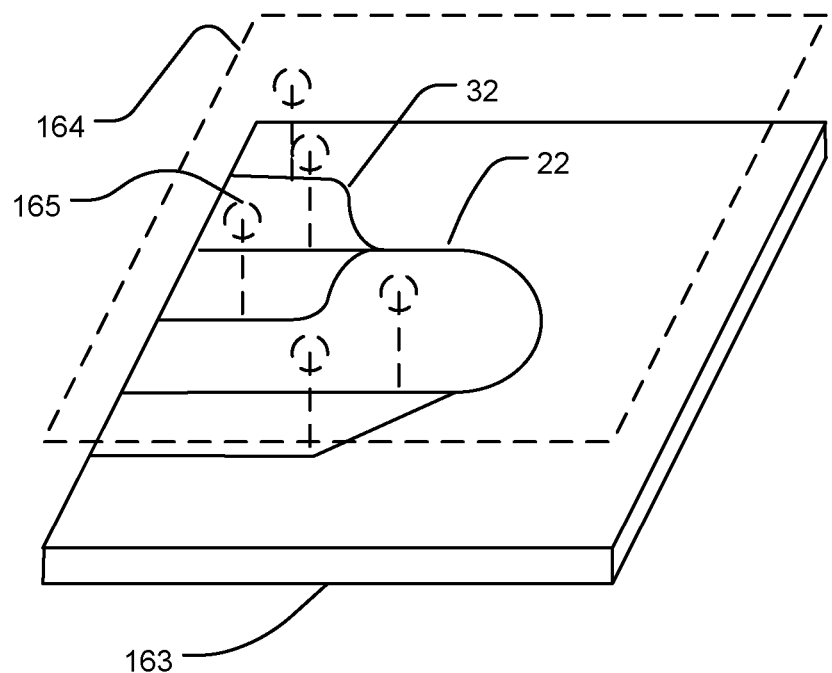
FIG. 22 is a schematic depiction of a particle detector apparatus comprising two substrates.
Figure 23:
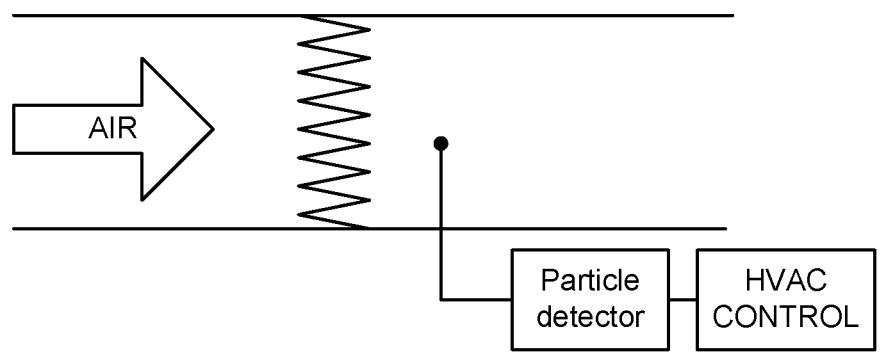
FIG. 23 illustrates an example application in the field of HVAC control.

In another example embodiment shown in FIG. 22, a particle detector according to an embodiment as described herein is connected to sample air downstream from a filter in an HVAC system. An output of the particle detector is connected to an HVAC supervisory control system. The HVAC control system may determine that a filter requires servicing or replacement based upon the output of the particle detector.

In another embodiment the particle detector is provided in a wearable form factor such as a form factor that can be carried in a pocket, mounted to a hat or backpack etc. The detector may compute cumulative exposure to particles in one or more size ranges and provide alarms when threshold exposures are reached. the particle detector may be battery powered. In some embodiments, the particle monitor is configured to maintain a log of detected particles or particle concentrations and to transmit that log to a monitoring station by way of a wireless link or to download that log to a monitoring station.

Where a component or feature is referred to above (e.g., shroud fluid, shroud gas, channel, microchannel, sub-channel, curved section, port, filter, light source, light sensor, sensor, flow sensor, pressure sensor, divider, source of pressurized fluid, pump, logic circuitry, controller, etc.), unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." Where the context permits, words in the above description using the singular or plural number may also include the plural or singular number respectively. The word "or," in reference to a list of two or more items, covers all of the following interpretations of the word: any of the items in the list, all of the items in the list, and any combination of the items in the list.

The above detailed description of example embodiments is not intended to be exhaustive or to limit this disclosure and claims to the precise forms disclosed above. While specific examples of, and examples for, embodiments are described above for illustrative purposes, various equivalent modifications are possible within the scope of the technology, as those skilled in the relevant art will recognize These and other changes can be made to the system in light of the above description. While the above description describes certain examples of the technology, and describes the best mode contemplated, no matter how detailed the above appears in text, the technology can be practiced in many ways. As noted above, particular terminology used when describing certain features or aspects of the system should not be taken to imply that the terminology is being redefined herein to be restricted to any specific characteristics, features, or aspects of the system with which that terminology is associated. In general, the terms used in the following claims should not be construed to limit the system to the specific examples disclosed in the specification, unless the above description section explicitly and restrictively defines such terms. Accordingly, the actual scope of the technology encompasses not only the disclosed examples, but also all equivalent ways of practicing or implementing the technology under the claims.

From the foregoing, it will be appreciated that specific examples of apparatus and methods have been described herein for purposes of illustration, but that various modifications, alterations, additions and permutations may be made without departing from the practice of the invention. The embodiments described herein are only examples. Those skilled in the art will appreciate that certain features of embodiments described herein may be used in combination with features of other embodiments described herein, and that embodiments described herein may be practised or implemented without all of the features ascribed to them herein. Such variations on described embodiments that would be apparent to the skilled addressee, including variations comprising mixing and matching of features from different embodiments, are within the scope of this invention.

As will be apparent to those skilled in the art in light of the foregoing disclosure, many alterations and modifications are possible in the practice of this invention without departing from the spirit or scope thereof. For example:

In some embodiments, particles are detected using a removable filter (e.g., a cartridge type filter) that is examined after being removed from the apparatus.

Forms of energy other than light which are attenuated by the presence of particles in a filter may be transmitted through a filter and sensed to determine an amount of particles present in a filter, such as, for example other types of electromagnetic radiation (such as x-rays, for example), ultrasound, and the like.

Presence of particles collected in a filter may be ascertained using gravimetric techniques (e.g., by vibrating the filter and determining one or more of resonant frequency, impedance, and displacement amplitude).

A curved section may comprise a non-planar curve, such as a ramped curve, corkscrew curve or the like.

Curved sections need not be smoothly curved. Embodiments may impart centrifugal forces using rectilinearly curved sections rather than smoothly curved section (e.g., sample fluid may be passed through a curved section that comprises two or more adjacent planar wall sections joined at angles). Such embodiments may achieve acceptable particle separation, so long as flow rates are maintained sufficiently low that significant secondary flows are avoided. It will be appreciated that a radius of curvature may be determined for rectilinearly curved sections.

A particle detector need not detect particles in a channel that is part of or integrated with the particle size separator.

Though example embodiments, simulations, experiments, and prototypes have been described using air and gas as working fluids, the invention may be practiced with other fluids.

While a number of exemplary aspects and embodiments have been discussed above, those of skill in the art will recognize certain modifications, permutations, additions and sub-combinations thereof. It is therefore intended that all such modifications, permutations, additions and sub-combinations are part of the invention and may be claimed in the claims of applications which claim priority to this application.

What is claimed is:

1. Size-specific aerosol detection apparatus comprising:
an aerosol size selector comprising:
a channel having a curved section,
a sample air or gas introduction port upstream of the curved section, and
at least one shroud air or gas port upstream of the curved section, the sample air or gas introduction port and the at least one shroud air or gas port configured to interpose first and second shroud air or gas streams respectively between a sample air or gas stream introduced via the sample air or gas introduction port and outside and inside walls of the curved section such that the sample air or gas stream is focused into a ribbon flowing between the shroud air or gas streams and flow of the sample air or gas stream and the shroud air or gas streams through the curved section exposes particles in the sample air or gas stream to centrifugal forces that act perpendicular to the flow of the sample air or gas stream and the shroud air or gas streams to spread aerosols of different sizes to different positions across the channel, and
a position-sensitive detector configured to detect aerosols in the channel downstream from a start of the curved section, the detector operable to detect aerosols passing at one or more specific positions across the channel corresponding to one or more corresponding particle sizes of interest.

2. Apparatus according to claim 1 wherein the at least one shroud air or gas port comprises an outside shroud air or gas port configured to introduce shroud air or gas along a side of the channel leading to the outside of the curved section.

3. Apparatus according to claim 2 wherein the outside shroud air or gas port is downstream from the sample air or gas introduction port.

4. Apparatus according to claim 1 wherein the at least one shroud air or gas port comprises an inside shroud air or gas port along a side of the channel leading to the inside of the curved section.

5. Apparatus according to claim 4 wherein the inside shroud air or gas port is downstream from the sample air or gas introduction port.

6. Apparatus according to claim 1 wherein the sample air or gas introduction port and the at least one shroud air or gas port are configured to interpose a shroud air or gas stream introduced via the at least one shroud air or gas port between a sample air or gas stream introduced via the sample air or gas introduction port and a first side of the channel between sides of the channel leading to the outside and inside of the curved section.

7. Apparatus according to claim 6 where the at least one shroud air or gas port comprises a first shroud air or gas port along the first side of the channel.

8. Apparatus according to claim 7 wherein the sample air or gas introduction port is on the first side of the channel and upstream the first shroud air or gas port.

9. Apparatus according to claim 8 wherein the at least one shroud air or gas port comprises a second shroud air or gas port upstream of the sample air or gas introduction port.

10. Apparatus according to claim 7 wherein the at least one shroud air or gas port comprises a second shroud air or gas port on a second side of the channel opposite the first side.

11. Apparatus according to claim 10 wherein the sample air or gas introduction port is upstream of the second shroud air or gas port.

12. Apparatus according to claim 1 comprising a source of pressurized shroud air or gas connected to the at least one shroud air or gas port.

13. Apparatus according to claim 12 wherein the source of pressurized shroud air or gas comprises an air pump and a filter connected to filter air pumped by the air pump.

14. Apparatus according to claim 12 wherein the source of pressurized shroud air or gas comprises a source of compressed air or gas.

15. Apparatus according to claim 1 comprising at least one downstream shroud air or gas port downstream of the curved section.

16. Apparatus according to claim 15 wherein the at least one downstream shroud air or gas port comprises a downstream outside shroud air or gas along a side of the channel extending from the outside of the curved section.

17. Apparatus according to claim 15 wherein the at least one downstream shroud air or gas port comprises a downstream inside shroud air or gas port on a side of the channel extending from the inside of the curved section.

18. Apparatus according to claim 15 comprising a source of pressurized shroud air or gas connected to the at least one downstream shroud air or gas port.

19. Apparatus according to claim 12 wherein the particle size selector comprises a variable valve operable to control flow of shroud air or gas from the source of pressurized shroud air or gas to the channel.

20. Apparatus according to claim 19 wherein the particle size selector comprises a plurality of variable valves operable to independently control flow of shroud air or gas from the source of pressurized shroud air or gas through corresponding ones of the at least one shroud air or gas port.

21. Apparatus according to claim 1 wherein a transverse width of the channel downstream from the curved section is wider than a transverse width of the channel in the curved section.

22. Apparatus according to claim 1 wherein the channel widens between the start of the curved section and the detector.

23. Apparatus according to claim 1 wherein the detector comprises a filter configured to collect particles entrained in gas flowing in the channel.

24. Apparatus according to claim 23 wherein at least a portion of the filter is translucent and wherein the detector comprises:
   a light source configured to illuminate at least a part of the translucent portion of the filter, and
   a light sensor configured to detect light transmitted by the filter.

25. Apparatus according to claim 24 wherein the filter comprises translucent and opaque transverse sections.

26. Apparatus according to claim 24 wherein the light source is configured to illuminate only one or more specific transverse sections of the filter.

27. Apparatus according to claim 24 wherein the light sensor is configured to detect only light transmitted through one or more specific transverse sections of the filter.

28. Apparatus according to claim 1 wherein the detector comprises a light source configured to emit a light beam into the channel and a light detector configured to detect light scattered by particles passing through the light beam.

29. Apparatus according to claim 28 wherein the light source is configured to illuminate only a specific transverse section of the channel.

30. Apparatus according to claim 28 wherein the light sensor is configured to sense only light scattered by particles passing through a specific transverse section of the channel.

31. Apparatus according to claim 1 wherein the channel has a fixed divider downstream of the curved section defining a plurality of sub-channels.

32. Apparatus according to claim 31 wherein the divider is generally parallel to an axis of curvature of the curved section.

33. Apparatus according to claim 31 wherein the detector is configured to detect only particles passing in one of the plurality of sub-channels.

34. Apparatus according to claim 31 wherein the divider is configured to separate a portion of air or gas flow adjacent a wall of the channel from a remainder of air or gas flow in the channel.

35. Apparatus according to claim 34 wherein the divider is generally perpendicular to an axis curvature of the curved section.

36. Apparatus according to claim 31 wherein one of the sub-channels has a second curved section downstream from the divider.

37. Apparatus according to claim 36 wherein a transverse width of the second curved section is greater than a transverse width of the one sub-channel's corresponding transverse section of the channel upstream from the divider.

38. Apparatus according to claim 1 wherein the detector is located downstream from a widening of the channel.

39. Apparatus according to claim 1 wherein the particle size selector comprises at least one variable valve operable to control at least one of flow of shroud air or gas into the channel and sample fluid into the channel.

40. Apparatus according to claim 39 where in the particle size selector comprises:
   a sensor configured to detect at least one of a flow rate and a pressure of air or gas in the channel, and
   a controller configured to control the variable valve to maintain laminar flow conditions in the channel based at least in part on the detected at least one of the flow rate and the pressure of the air or gas in the channel.

41. Apparatus according to claim 39 wherein the at least one shroud air or gas port comprises:
   an outside shroud air or gas port along a side of the channel leading to the outside of the curved section, and
   an inside shroud air or gas port along a side of the channel leading to the inside of the curved section,
   and wherein the at least one variable valve comprises a variable shroud control valve operable to control flow of shroud air or gas introduced via one of the outside shroud air or gas port and the inside shroud air or gas port.

42. Apparatus according to claim 41 wherein particle size selector comprises a variable valve operable to control flow of shroud air or gas introduced via the other one of the outside shroud air or gas port and the inside shroud air or gas port.

43. Apparatus according to claim 41 wherein the particle size selector comprises:
   a shroud flow sensor configured to detect at least one of a flow rate and a pressure of shroud air or gas flow controlled by the variable shroud control valve, and
   a controller configured to control the variable shroud control valve based at least in part on the at least one of the flow rate and the pressure of shroud air or gas detected by the shroud flow sensor.

44. Apparatus according to claim 43 wherein the controller is configured to control the variable shroud flow valve to steer flow of sample air or gas introduced via the sample air or gas introduction port to a specific transverse section of the channel.

45. Apparatus according to claim 1 wherein the channel comprises a planar channel.

46. Apparatus according to claim 1 wherein the channel comprises a non-planar channel.

47. Apparatus according to claim 1 wherein the channel has a rectangular cross section.

48. Apparatus according to claim 47 wherein the transverse width of the channel is larger than the vertical dimension of the channel.

49. Apparatus according to claim 1 wherein the transverse width of the channel upstream from the curved section is in a range of 200 μm±140 μm.

50. Apparatus according to claim 1 wherein the transverse width of the channel upstream from the curved section is less than 1 mm.

51. Apparatus according to claim 1 wherein the hydraulic diameter of the channel upstream from the curved section is at least 100 μm.

52. Apparatus according to claim 1 wherein the curved section turns at least 90 degrees.

53. Apparatus according to claim 1 wherein the curved section turns at least 120 degrees.

54. Apparatus according to claim 1 wherein the curved section turns at least 180 degrees.

55. Apparatus according to claim 1 wherein a radius of curvature of the curved section is greater than 1 mm.

56. Apparatus according to claim 1 wherein a radius of curvature of the curved section is less than 5 cm.

57. Apparatus according to claim 1 wherein the height of the channel upstream from the curved section is in a range of 200 μm±140 μm.

58. Apparatus according to claim 1 wherein the transverse width of the channel downstream from the curved section is at least 5 times as wide as the width of the channel within the curved section.

59. Portable and personal air quality monitoring apparatus comprising apparatus according to claim 1.

* * * * *